United States Patent
Wagner et al.

(10) Patent No.: US 8,784,853 B2
(45) Date of Patent: Jul. 22, 2014

(54) STABILIZATION OF HOUSEHOLD, BODY-CARE AND FOOD PRODUCTS BY USING BENZOTROPOLONE CONTAINING PLANT EXTRACTS AND/OR RELATED BENZOTROPOLONE DERIVATIVES

(75) Inventors: Barbara Wagner, Lörrach (DE); Oliver Reich, Limburgerhof (DE); Alexander Mantler, Rheinfelden-Karsau (DE); Reinhold Öhrlein, Rheinfelden-Herten (DE); Walter Fischer, Reinach (CH); Albert Schneider, Grenzach-Wyhlen (DE)

(73) Assignee: BASF SE, Ludwigshafen (DE)

( * ) Notice: Subject to any disclaimer, the term of this patent is extended or adjusted under 35 U.S.C. 154(b) by 97 days.

(21) Appl. No.: 13/499,706

(22) PCT Filed: Oct. 5, 2010

(86) PCT No.: PCT/EP2010/064809
§ 371 (c)(1),
(2), (4) Date: Jun. 4, 2012

(87) PCT Pub. No.: WO2011/042423
PCT Pub. Date: Apr. 14, 2011

(65) Prior Publication Data
US 2012/0230925 A1    Sep. 13, 2012

(30) Foreign Application Priority Data

Oct. 6, 2009  (EP) .................................. 09172338
Nov. 13, 2009 (EP) .................................. 09175892

(51) Int. Cl.
*A61K 8/02* (2006.01)
*C07F 15/00* (2006.01)

(52) U.S. Cl.
USPC ........... 424/401; 568/300; 568/308; 568/327; 568/717

(58) Field of Classification Search
USPC ................ 424/401; 568/300, 308, 327, 717
See application file for complete search history.

(56) References Cited

U.S. PATENT DOCUMENTS

| 2,770,545 | A | 11/1956 | Thompson |
| 7,087,790 | B2 * | 8/2006 | Ho et al. ................ 568/311 |
| 2003/0157035 | A1 | 8/2003 | Chaudhuri |
| 2005/0049284 | A1 | 3/2005 | Ho et al. |
| 2007/0219275 | A1 | 9/2007 | Baschong |
| 2011/0123468 | A1 | 5/2011 | Wagner et al. |

FOREIGN PATENT DOCUMENTS

| WO | 2005/094772 A2 | 10/2005 |
| WO | 2008/003529 A1 | 1/2008 |
| WO | 2009/156324 A2 | 12/2009 |

OTHER PUBLICATIONS

Dixon et al. Journal of the Chemical Society, Perkin Transactions 2: Physical Organic Chemistry (1974): 12, 1430-3.*

* cited by examiner

*Primary Examiner* — Lezah Roberts
*Assistant Examiner* — Nannette Holloman
(74) *Attorney, Agent, or Firm* — Shiela A. Loggins

(57) ABSTRACT

Disclosed is the use of benzotropolone derivatives of formula (1), wherein $R_1$, $R_2$ and $R_7$ independently from each other are hydrogen; $C_1$-$C_3$alkyl; or $COR_8$; $R_3$ is hydrogen; or $COOR_9$ $R^4$ is hydrogen; or $C_1$-$C_3$alkyl; $R_5$ is hydrogen; hydroxy; $C_1$-$C_3$-alkoxy; or -O-(CO)—$R_{10}$; $R_6$ is hydrogen; $C_1$-$C_3$alkyl; or $COR_8$; or $R_5$ and $R_6$ together may form a five or six membered ring; or $R_6$ and $R_7$ together form a five or six membered ring; and $R_8$, $R_9$, $R_{10}$ independently of each other are $C_1$-$C_{30}$alkyl; for protecting body-care and household products from photolytic and oxidative degradation.

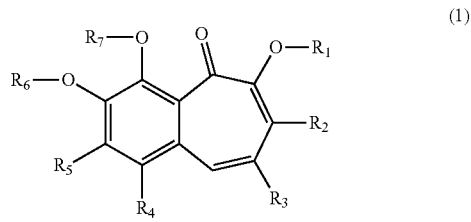

(1)

15 Claims, No Drawings

STABILIZATION OF HOUSEHOLD, BODY-CARE AND FOOD PRODUCTS BY USING BENZOTROPOLONE CONTAINING PLANT EXTRACTS AND/OR RELATED BENZOTROPOLONE DERIVATIVES

The present invention relates to the use of selected light stabilizers for protecting body-care and household products from photolytic and oxidative degradation.

The product trend of recent years towards increased use of natural substances based on oil and fat in cosmetic formulations and household products also increases the problem of the oxidative degradation of fats and oils, resulting in rancidity. Natural oils or unsaturated fatty acids are hardly ever absent from emulsions. Oxidative changes may sometimes produce reactive metabolites, for example ketones, aldehydes, acids, epoxides and lipoperoxides.

As a result there is on the one hand an undesirable change in the smell of the products and on the other hand substances are prone to deteriorate which may alter the skin tolerance. The uncontrolled formation of free radicals on the skin contributes primarily to the initiation and progression of a multitude of pathophysical modulations, for example allergies, inflammation, cancerogenesis and the like.

However, oxidative degradation processes are not only found in the case of natural substances based on oil and fat. They are also found in a number of other cosmetic ingredients, such as fragrances and odoriferous substances, vitamins, colourants and the like.

To prevent oxidative degradation processes (photooxidation, autooxidation), so-called antioxidants (AO) are therefore used in cosmetic and food products. These antioxidants may be classified into compounds which prevent oxidation (complex formers, reducing agents and the like) and into compounds which interrupt the free radical chain reactions, for example butylated hydroxytoluene (BHT), butylated hydroxyanisol (BHA), gallates, such as propylgallate (PG), or t-butylhydroquinone (TBHQ). However, the latter compounds often do not meet the requirements with respect to pH stability as well as to light and temperature stability.

As a consequence the actives in such containers unadvantageously change their properties due to autoxidative processes. This results for example in a reduction of viscosity and changes in color or smell.

Furthermore, the growing product trend in the recent years has also resulted in an increased use of transparent (glass, PET etc.) containers for cosmetic formulations and household products. Although both glass and ordinary plastics have a certain inherent absorption in the UV-B-range the absorption in the UV-A range is very low.

Various stabilization techniques for clear packaged products by UV absorption are commonly used and well known. For example broad-band UV light stabilizers of the benzotriazole class enhance product stability and shelf live due to their very good UV-A and UV-B absorption properties compared to other absorbers such as benzophenones which mainly absorb UV-B. The most effective stabilizers known today for preventing or delaying light induced fading of transparent packaged products are e.g. benzotriazole derivatives registered under the trade names BASF TINOGARD HS or BASF TINOGARD TL.

It would be now advantageously to combine anti-oxidant and radical-scavenging as well as photoprotective properties in one stabilizer molecule.

Surprisingly, it has been found that specific light stabilizers based on benzotropolone derivatives perform outstanding UV absorber as well as antioxidant properties and are therefore suitable for product protection.

Polyphenols based on the benzotropolone moiety can be isolated from plants or fungi. Examples of naturally occurring benzotropolones are purpurogallin, purpurogallin carboxylic acid, fomentariol from the fungus *Fomes fomentarius*, goupiolone and aurantricholone from the fungus *Tricholoma aurantium*. Theaflavins which are present in black tea is another well known group of polyphenols which contain a benzotropolone nucleus.

Synthetic benzotropolones are produced by an oxidative coupling of a 1,2-dihydroxybenzene derivative with a 1,2,3-trihydroxybenzene derivative.

The synthetic and naturally occurring benzotropolone compounds have in common that they are effective and photostable UV absorbers with strong antioxidant properties and therefore are suitable to be used as stabilizers.

Therefore, the present invention relates to the use of benzotropolone derivatives of formula

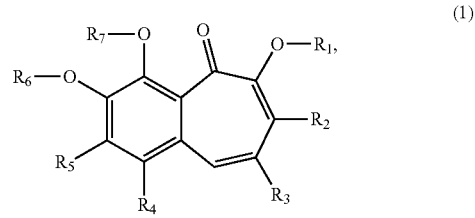

(1)

wherein
$R_1$, $R_2$ and $R_7$ independently from each other are hydrogen; $C_1$-$C_{30}$alkyl; or $COR_8$;
$R_3$ is hydrogen; or $COOR_9$;
$R_4$ is hydrogen; or $C_1$-$C_{30}$alkyl;
$R_5$ is hydrogen; hydroxy; $C_1$-$C_{30}$-alkoxy; or —O—(CO)—$R_{10}$;
$R_6$ is hydrogen; $C_1$-$C_{30}$alkyl; or $COR_8$; or
$R_5$ and $R_6$ together may form a five or six membered ring; or $R_6$ and $R_7$ together form a five or six membered ring; and
$R_8$, $R_9$, $R_{10}$ independently of each other are $C_1$-$C_{30}$alkyl;
for protecting body-care and household products from photolytic and oxidative degradation.

Preferred are compounds of formula (1), wherein
$R_1$ is hydrogen; $COR_8$; or $C_1$-$C_{30}$alkyl
$R_2$, $R_4$ and $R_5$ are hydrogen;
$R_3$ is $COOR_9$;
$R_6$ and $R_7$ independently from each other are hydrogen; $C_1$-$C_{30}$alkyl; or $COR_8$; or
$R_6$ and $R_7$ together form a five or six membered ring; and
$R_8$ is defined as in formula (1).

More preferred are compounds of formula (1), wherein
$R_1$ is hydrogen; or CO—$CH_3$;
$R_2$, $R_4$ and $R_5$ are hydrogen;
$R_3$ is COO—$C_3H_7$;
$R_6$ and $R_7$ independently from each other are hydrogen; or CO—$CH_3$; or
$R_6$ and $R_7$ together form a five or six membered ring.

Also preferred are compounds of formula (1), wherein
$R_1$, $R_2$ and $R_7$ independently from each other are hydrogen; methyl; or —CO—$CH_3$;
$R_3$ is hydrogen; or —$COOR_9$;
$R_4$ is hydrogen; or $C_1$-$C_{30}$alkyl;
$R_5$ is hydrogen; methoxy; or —O—(CO)—$CH_3$;
$R_6$ is hydrogen; methyl; or —CO—$CH_3$; or
$R_5$ and $R_6$ together may form a five or six membered ring; or $R_6$ and $R_7$ together form a five or six membered ring; and
$R_9$ is $C_1$-$C_{10}$alkyl.

Most preferred are the compounds of the formulae

-continued

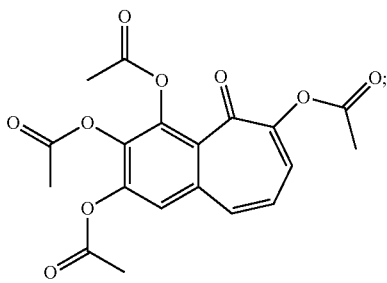
(B-44)

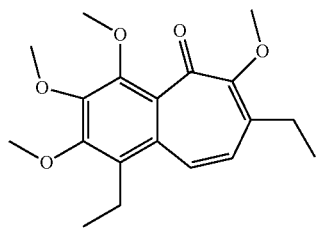
(B-45)

; and

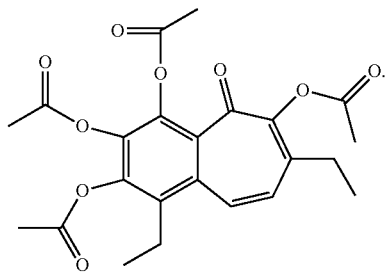
(B-46)

Further examples of the benzotropolones used for the present invention are the compounds

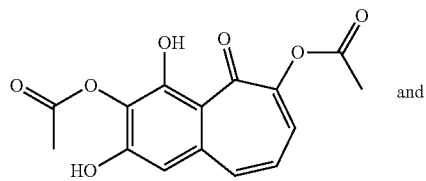
(B-32)

and

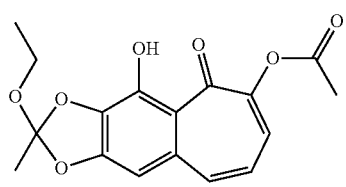
(B-37)

$C_1$-$C_{30}$alkyl are straight chain or branched radicals like methyl, ethyl, n-propyl, isopropyl, n-butyl, sek-butyl, tert-butyl, amyl, isoamyl or tert-amyl, hexyl, 2-ethylhexyl, heptyl, octyl, isooctyl, nonyl, decyl, undecyl, dodecyl, tetradecyl, undecyl, eicosyl, tetracosyl, pentacosyl, heptacosyl, octacosyl or triacontyl.

$C_1$-$C_{30}$alkoxy are straight chain or branched radicals like methoxy, ethoxy, n-propoxy, or iso-propoxy, isopropyloxy, n-butyloxy, sek-butyloxy, tert-butyloxy, amyloxy, isoamyloxy or tert-amyloxy, hexyloxy, 2-ethylhexyloxy, heptyloxy, octyloxy, isooctyloxy, nonyloxy, decyloxy, undecyloxy, dodecyloxy, tetradecyloxy, undecyloxy, eicosyloxy, tetracosyloxy, pentacosyloxy, heptacosyloxy, octacosyloxy or triacontyloxy.

Each alkyl can be saturated or unsaturated.

Each alkyl may be substituted by one or more E and/or interrupted by one or more D.

D is —CO—; —COO—; —O—; —S—; —$CR_{12}$=$CR_{13}$—; or —C≡C—; and

E is —$OR_{18}$; —$NR_{14}R_{15}$; —$COR_{17}$; —$COOR_{16}$ or —$CONR_{14}R_{15}$; wherein $R_{12}$, $R_{13}$, $R_{14}$ and $R_{15}$ are independently of each other are hydrogen; $C_6$-$C_{18}$aryl which is optionally substituted by OH, $C_1$-$C_{18}$alkyl or $C_1$-$C_{18}$alkoxy; $C_1$-$C_{18}$alkyl, which is optionally interrupted by —O—; or $R_{14}$ and $R_{15}$ together form a five or six membered ring, $R_{16}$ is hydrogen; $C_6$-$C_{18}$aryl which is optionally substituted by OH, $C_1$-$C_{18}$alkyl or $C_1$-$C_{18}$alkoxy; $C_1$-$C_{18}$alkyl which is optionally interrupted by —O—;

$R_{17}$ is H; $C_6$-$C_{18}$aryl which is optionally substituted by OH, $C_1$-$C_{18}$alkyl or $C_1$-$C_{18}$alkoxy; or $C_1$-$C_{18}$alkyl which is optionally interrupted by —O—;

$R_{18}$ is hydrogen; $C_6$-$C_{18}$aryl which is optionally substituted by OH, $C_1$-$C_{18}$alkyl or $C_1$-$C_{18}$alkoxy; or $C_1$-$C_{18}$alkyl which is optionally interrupted by —O—.

The compounds of formulae (1) can be present in their protonated or deprotonated form.

The benzotropolone derivatives as used in the present invention represent known and novel compounds.

The novel compounds correspond to formula

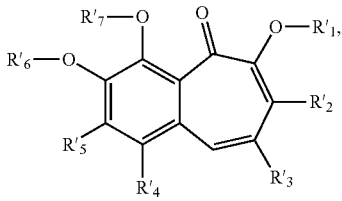
(1')

wherein $R'_1$, $R'_2$ and $R'_7$ independently from each other are hydrogen; $C_1$-$C_{30}$alkyl; or $COR_8$;

$R'_3$ is hydrogen; or $COOR_9$;

$R'_4$ is hydrogen; or $C_1$-$C_{30}$alkyl;

$R'_5$ is hydrogen; hydroxy; $C_1$-$C_{30}$-alkoxy; or —O—(CO)—$R_{10}$;

$R'_6$ is hydrogen; $C_1$-$C_{30}$alkyl; or $COR_8$; or $R'_5$ and $R'_6$ together may form a five or six membered ring; or $R'_6$ and $R'_7$ together form a five or six membered ring; and $R'_8$, $R'_9$, $R'_{10}$ independently of each other are $C_1$-$C_{30}$alkyl;

with the proviso that in the compounds of formula (1') either $R_7$ and $R_8$ together form a five or six membered ring; or $R_6$ and $R_7$ together form a five or six membered ring.

Preferred are compounds of formula (1'), wherein $R_3$ is a radical of formula

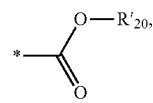

wherein $R'_{20}$ is $C_3$-$C_{30}$alkyl $R'_5$ is hydrogen; or $C_1$-$C_{12}$alkyl;

$R'_1$, $R'_6$ and $R'_7$ are hydrogen; $COR'_9$; or $C_1$-$C_{30}$alkyl; and $R'_9$ is defined as in formula (1').

Preferred are also compounds correspond to formula

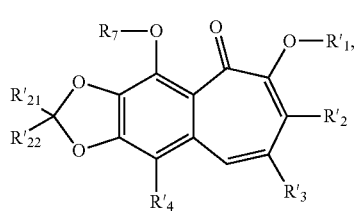

(2')

wherein

R'$_{21}$ and R'$_{22}$ independently of one another are hydrogen; OH; C$_1$-C$_{30}$alkyl; or C$_1$-C$_{30}$alkoxy; and R'$_1$, R'$_2$, R'$_3$, R'$_4$, and R'$_7$ are defined as in formula (1').

Preferred are also compounds of formula

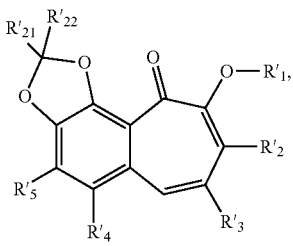

(3')

wherein

R'$_{21}$ and R'$_{22}$ independently of one another are hydrogen; OH; C$_1$-C$_{30}$alkyl; or C$_1$-C$_{30}$alkoxy;

R'$_1$, R'$_2$, R'$_3$, R'$_4$ and R'$_5$ are defined as in formula (1').

More preferred are compounds of formula (3'), wherein

R'$_{21}$ and R'$_{22}$ independently of one another are hydrogen; OH; unsubstituted C$_1$-C$_{30}$alkyl or unsubstituted C$_1$-C$_{30}$alkoxy; and R'$_1$, R'$_2$, R'$_3$, R'$_4$ and R'$_5$ are defined as in formula (1').

Further novel compounds correspond to formula (3') wherein

R$_3$ is a radical of formula

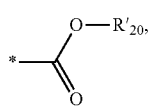

wherein

R'$_{20}$ is C$_3$-C$_{30}$alkyl;

R'$_5$ is hydrogen; or C$_1$-C$_{12}$alkyl;

R'$_1$, R'$_6$ and R'$_7$ are hydrogen, COR'$_9$; or C$_1$-C$_{30}$alkyl; and

R'$_9$ is defined as in formula (1').

Further novel compounds correspond to formula

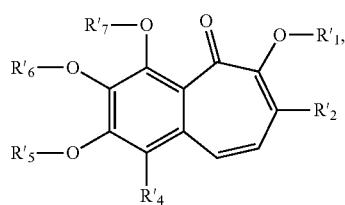

(4')

wherein

R'$_2$ and R'$_4$ independently from each other are C$_1$-C$_{30}$alkyl;

R'$_1$, R'$_5$, R'$_6$ and R'$_7$ are C$_1$-C$_{30}$alkyl; or COR$_8$; and

R'$_8$ is defined as in formula (1').

Preferred are also compounds of formula

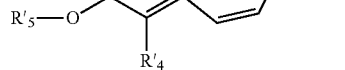

(5')

wherein

R'$_3$ is a radical of formula

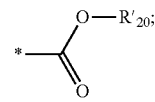

R'$_{20}$ is C$_3$-C$_{30}$alkyl;

R'$_1$, R'$_6$ and R'$_7$ are hydrogen; COR$_S$; or C$_1$-C$_{30}$alkyl; and

R'$_9$ is C$_1$-C$_{30}$alkyl.

The benzotropolone derivatives according to the present invention are isolated from natural sources like from a plant extract and/or those synthesized by chemical oxidation of specific precursor compounds such as pyrogallol derivatives and 1,2-dihydroxy-benzene derivatives.

The benzotropolone derivatives of formula (1) as well as mixtures of these compounds with other UV absorbers as listed in Tables 1-3, phenolic or non-phenolic antioxidants or with complex formers are particularly suitable for protecting body-care and household products against photolytic degradation.

Examples of organic UV filters that can be used in admixture with the compounds of formula (1) are listed in the following Table:

TABLE 1

Suitable UV filter substances which can be additionally used with the compounds of formula (1)

p-aminobenzoic acid derivatives, for example 4-dimethylaminobenzoic acid 2-ethylhexyl ester;
salicylic acid derivatives, for example salicylic acid 2-ethylhexyl ester;
benzophenone derivatives, for example 2-hydroxy-4-methoxybenzophenone and its 5-sulfonic acid derivative;
diphenylacrylates, for example 2-ethylhexyl 2-cyano-3,3-diphenylacrylate, and 3-(benzofuranyl) 2-cyanoacrylate;

TABLE 1-continued

Suitable UV filter substances which can be additionally used with the compounds of formula (1)

3-imidazol-4-ylacrylic acid and esters;
benzofuran derivatives, especially 2-(p-aminophenyl)benzofuran derivatives, described in
EP-A-582 189, U.S. Pat. No. 5,338,539, U.S. Pat. No. 5,518,713 and EP-A-613 893;
polymeric UV absorbers, for example the benzylidene malonate derivatives described in
EP-A-709 080;
camphor derivatives, for example 3-(4'-methyl)benzylidene-bornan-2-one, 3-benzylidene-
bornan-2-one, N-[2(and 4)-2-oxyborn-3-ylidene-methyl)-benzyl]acrylamide polymer, 3-(4'-
trimethylammonium)-benzylidene-bornan-2-one methyl sulfate, 3,3'-(1,4-phenylenedi-
methine)-bis(7,7-dimethyl-2-oxo-bicyclo[2.2.1]heptane-1-methanesulfonic acid) and salts,
3-(4'-sulfo)benzylidene-bornan-2-one and salts; camphorbenzalkonium methosulfate;
hydroxyphenyltriazine compounds, for example 2-(4'-methoxyphenyl)-4,6-bis(2'-hydroxy-4'-
n-octyloxyphenyl)-1,3,5-triazine; 2,4-bis{[4-(3-(2-propyloxy)-2-hydroxy-propyloxy)-2-hydroxy]-
phenyl}-6-(4-methoxyphenyl)-1,3,5-triazine; 2,4-bis{[4-(2-ethyl-hexyloxy)-2-hydroxy]-
phenyl}-6-[4-(2-methoxyethyl-carboxyl)-phenylamino]-1,3,5-triazine; 2,4-bis{[4-(tris-
(trimethylsilyloxy-silylpropyloxy)-2-hydroxy]-phenyl}-6-(4-methoxyphenyl)-1,3,5-triazine;
2,4-bis{[4-(2''-methylpropenyloxy)-2-hydroxy]-phenyl}-6-(4-methoxyphenyl)-1,3,5-triazine;
2,4-bis{[4-(1',1',1',3',5',5',5'-heptamethyltrisilyl-2''-methyl-propyloxy)-2-hydroxy]-phenyl}-6-
(4-methoxyphenyl)-1,3,5-triazine; 2,4-bis{[4-(3-(2-propyloxy)-2-hydroxy-propyloxy)-2-
hydroxy]-phenyl}-6-[4-ethylcarboxy)-phenylamino]-1,3,5-triazine;
benzotriazole compounds, for example 2,2'-methylene-bis(6-(2H-benzotriazol-2-yl)-4-
(1,1,3,3-tetramethylbutyl)-phenol;
trianilino-s-triazine derivatives, for example 2,4,6-trianiline-(p-carbo-2'-ethyl-1'-oxy)-1,3,5-
triazine and the UV absorbers disclosed in U.S. Pat. No. 5,332,568, EP-A-517 104, EP-A-507 691,
WO 93/17002 and EP-A-570 838;
2-phenylbenzimidazole-5-sulfonic acid and salts thereof;
menthyl o-aminobenzoates;
physical sunscreens coated or not as titanium dioxide, zinc oxide, iron oxides, mica, MnO,
$Fe_2O_3$, $Ce_2O_3$, $Al_2O_3$, $ZrO_2$. (surface coatings: polymethylmethacrylate, methicone
(methylhydrogenpolysiloxane as described in CAS 9004-73-3), dimethicone, isopropyl
titanium triisostearate (as described in CAS 61417-49-0), metal soaps as magnesium
stearate (as described in CAS 4086-70-8), perfluoroalcohol phosphate as C9-15
fluoroalcohol phosphate (as described in CAS 74499-44-8; JP 5-86984, JP 4-330007)).
The primary particle size is an average of 15 nm-35 nm and the particle size in dispersion is
in the range of 100 nm-300 nm.
aminohydroxy-benzophenone derivatives disclosed in DE 10011317, EP 1133980 and EP
1046391
phenyl-benzimidazole derivatives as disclosed in EP 1167358
the UV absorbers described in "Sunscreens", Eds. N. J. Lowe, N. A. Shaath, Marcel Dekker,
Inc., New York and Basle or in Cosmetics & Toiletries (107), 50ff (1992) also can be used
as additional UV protective substances.

TABLE 2

Suitable UV filter substances which can be additionally used with the UV absorbers according to the present invention

| | |
|---|---|
| DE 10013318 | T 1 pp 8-9, all Examples pp 10-13, T 2 pp 13-14, all Examples p 14, Ex A, B, C, D, E, F pp 19-20 |
| DE 10206562 A1 | Ex 1-3 p 10, Ex 4-7 p 11, Ex 8-15 pp 12-14 |
| DE 10238144 A1 | Ex on p 3-5; |
| DE 10331804 | T 1 p 4, T 2 + 3 p 5 |
| DE 19704990 A1 | Ex 1-2 on pp 6-7; |
| EP 613 893 | Ex 1-5 + 15, T 1, pp 6-8 |
| EP 0 998 900 A1 | Ex on pp 4-11 |
| EP 1 000 950 | Comp. In Table 1, pp 18-21 |
| EP 1 005 855 | T 3, p 13 |
| EP 1 008 586 | Ex 1-3, pp 13-15 |
| EP 1 008 593 | Ex 1-8, pp 4-5 |
| EP 1 027 883 | Compound VII, p 3 |
| EP 1 027 883 | Comp. I-VI, p 3 |
| EP 1 028 120 | Ex 1-5, pp 5-13 |
| EP 1 059 082 | Ex 1; T 1, pp 9-11 |
| EP 1 060 734 | T 1-3, pp 11-14 |
| EP 1 064 922 | Compounds 1-34, pp 6-14 |
| EP 1 077 246 A2 | Ex 1-16 on pp 5-11; |
| EP 1 081 140 | Ex 1-9, pp 11-16 |
| EP 1 103 549 | Compounds 1-76, pp 39-51 |
| EP 1 108 712 | 4,5-Dimorpholino-3-hydroxypyridazine |
| EP 1 123 934 | T 3, p 10 |
| EP 1 129 695 | Ex 1-7, pp 13-14 |
| EP 1 167 359 | Ex 1, p 11 and Ex 2, p 12 |
| EP 1 232 148 B1 | Ex 4-17 on pp 3-5; |
| EP 1 258 481 | Ex 1, pp 7, 8 |
| EP 1 310 492 A1 | Ex 1-16 on pp 22-30 |
| EP 1 371 654 A1 | Ex on pp 5-7 |
| EP 1 380 583 A2 | Ex 1, p 6; |
| EP 1 423 351 A2 | Ex 1-16 on pp 31-37; |
| EP 1 423 371 A1 | T 1 on pp 4-8, Ex on p 9, Ex 1-9 on pp 36-42; |
| EP 1 454 896 A1 | Ex 1-5 on pp 10-13, Examples on pp 4-5; |
| EP 1 471 059 A1 | Ex 1-5 on pp 4-5; |
| EP 1484051 A2 | Formula III-VII on pp18-19, Ex 7-14 on pp 7-9, Ex 18-23 on pp 11-12, Ex 24-40 on pp 14-17; |
| EP 420 707 B1 | Ex 3, p 13 (CAS Reg. No 80142-49-0) |
| EP 503 338 | T 1, pp 9-10 |
| EP 517 103 | Ex 3, 4, 9, 10 pp 6-7 |
| EP 517 104 | Ex 1, T 1, pp 4-5; Ex 8, T 2, pp 6-8 |
| EP 626 950 | all compounds |
| EP 669 323 | Ex 1-3, p 5 |
| EP 743 309 A1 | Ex 1-12 on pp 18-24; |
| EP 780 382 | Ex 1-11, pp 5-7 |
| EP 823 418 | Ex 1-4, pp 7-8 |
| EP 826 361 | T 1, pp 5-6 |
| EP 832 641 | Ex 5 + 6 p 7; T 2, p 8 |
| EP 832 642 | Ex 22, T 3, pp 10-15; T 4, p 16 |
| EP 852 137 | T 2, pp 41-46 |
| EP 858 318 | T 1, p 6 |
| EP 863 145 | Ex 1-11, pp 12-18 |
| EP 878 469 A1 | T 1, pp 5-7; |
| EP 895 776 | Comp. In rows 48-58, p 3; R 25 + 33, p 5 |
| EP 911 020 | T 2, pp 11-12 |
| EP 916 335 | T 2-4, pp 19-41 |

TABLE 2-continued

Suitable UV filter substances which can be additionally used with the UV absorbers according to the present invention

| | |
|---|---|
| EP 924 246 | T 2, p 9 |
| EP 933 376 | Ex 1-15, pp 10-21 |
| EP 944 624 | Ex 1 + 2, pp 13-15 |
| EP 945 125 | T 3 a + b, pp 14-15 |
| EP 95 097 | Ex 1, p 4 |
| EP 967 200 | Ex 2; T 3-5, pp 17-20 |
| EP 969 004 | Ex 5, T 1, pp 6-8 |
| FR 2842806 A1 | Ex I p 10, Ex II p 12 |
| FR 2861075 A1 | Ex 1-3 on pp 12-14; |
| FR 2862641 | Formula 3 on p4; Ex A-J on pp 7-9; |
| KR 2004025954 | all kojyl benzoate derivatives |
| JP 06135985 A2 | Formula 1 on p 2; Ex 1-8 on pp 7-8; |
| JP 2000319629 | CAS Reg Nos. 80142-49-0, 137215-83-9, 307947-82-6 |
| JP 2003081910 A | Ex on p 1; |
| JP 3686911 B2 | All benzylidene-gamma-butyrolactone derivatives |
| US 2003/0053966A1 | Ex on pp 3-6 |
| US 2004057912 A1 | Ex on p 7-9, Ex 1 on p 10; |
| US 2004057914 A1 | Ex on p 8-12, Ex 1 on p 12; |
| US 2004/0057911A1 | Formula I and II on p 1; formula III and IV on p3; Ex 1-3 on pp 5-6; |
| US 2004/0071640A1 | Ex 1-12 on pp 4-7; |
| US 2004/0091433A1 | Ex 1-6 on pp 14-16; |
| US 2004/0136931A1 | Ex 1-3 on p 7; |
| US 2004/0258636A1 | Ex 1-11 on pp 9-15; |
| US 2005/0019278A1 | Ex 1-9 on pp 6-8; |
| US 2005/0136012A1 | Formula 1 on p 2; |
| US 2005/0136014A1 | Formula a-c on p 2; Examples on p 3; |
| US 2005/0201957A1 | Formula 1 on p1; Ex A, B, C, D, E, F, G on pp 2-3; |
| US 2005/0249681A1 | all compounds on pp 2-3, Ex 1 on p 6; |
| U.S. Pat. No. 5,635,343 | all compounds on pp 5-10 |
| U.S. Pat. No. 5,332,568 | Ex 1, p 5, T 1 + 2, pp 6-8 |
| U.S. Pat. No. 5,338,539 | Ex 1-9, pp 3 + 4 |
| U.S. Pat. No. 5,346,691 | Ex 40, p 7; T 5, p 8 |
| U.S. Pat. No. 5,801,244 | Ex 1-5, pp 6-7 |
| U.S. Pat. No. 6,613,340 | Ex I, II pp 9-11, Examples on rows 28-53 p 6 |
| U.S. Pat. No. 6,800,274 B2 | Formulas I-VI and IX-XII on pp 14-18; |
| U.S. Pat. No. 6,890,520 B2 | Ex 1-10 on pp 6-9; |
| U.S. Pat. No. 6,926,887 B2 | Ex A on pp5/6; Formulas I-VIII on pp 27-29; |
| U.S. Pat. No. 6,936,735 B2 | Formula 1-2 on p 2; formula 3-4 on p 6; |
| WO 0149686 | Ex 1-5, pp 16-21 |
| WO 0168047 | Tables on pp 85-96 |
| WO 0181297 | Ex 1-3, pp 9-11 |
| WO 0191695 | Formula I on p 4, T on p 8 |
| WO 0202501 A1 | Ex Ia-c, p 5 |
| WO 02069926 A1 | Ex on p 9, Ex on pp 17-23 |
| WO 02072583 | T on pp 68-70 |
| WO 02080876 | Ex 1 on pp 7-9 |
| WO 0238537 | All compounds p 3, compounds on rows 1-10 p 4 |
| WO 03004557 A1 | Ex A1-A29 on pp 36-57; |
| WO 03007906 | Ex I-XXIII, pp 42-48 |
| WO 03086341 A2 | Formula 2-21, pp 4-6; |
| WO 03092643 A1 | T on pp 34-35, compounds listed on p 16 |
| WO 03097577 A1 | Ex on pp 6-8; Ex 1-3 on pp 15-18; |
| WO 03104183 A1 | Formula I-IV on p 1; Ex 1-5 on pp 27-28; |
| WO 04000256 A1 | Ex 1-10 on pp 18-24 |
| WO 04020398 A1 | Ex 1-3 on pp 14-17 |
| WO 04020398 A1 | Formulas I-VI on pp 21-24, Formula IX on p 25; |
| WO 05009938 A2 | Formula I on p 1; Ex 1-2 on pp 14-15; |
| WO 05065154 A2 | Formula a-c on pp 5-6; |
| WO 05080341 A1 | Formula 1 on p 3; Examples on pp 9-13; |
| WO 9217461 | Ex 1-22, pp 10-20 |
| WO 9220690 | Polymeric Comp in Examples 3-6 |
| WO 9301164 | T 1 + 2, pp 13-22 |
| WO 9714680 | Ex 1-3, p 10 |

(Abbreviations T: Table, R: row, Comp: compound, Ex: compound(s) of Patent Example, p: page; the generic scope of the UV absorbers is described in the left-hand column; specific compounds are indicated in the right-hand column)

TABLE 3

Suitable UV filter substances and adjuvants which can be additionally used with the compounds of formula (1)

| No. | Chemical Name | CAS No. |
|---|---|---|
| 1 | (+/−)-1,7,7-trimethyl-3-[(4-methylphenyl)methylene]bicyclo[2.2.1]-heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts; Mexoryl SL | 56039-58-8 |
| 11 | 1-[4-(1,1-dimethylethyl)phenyl]-3-(4-methoxyphenyl)propane-1,3-dione; avobenzone | 70356-09-1 |
| 12 | Methyl N,N,N-trimethyl-4-[(4,7,7-trimethyl-3-oxobicyclo[2,2,1]hept-2-ylidene)methyl]anilinium sulphate; Mexoryl SO | 52793-97-2 |
| 22 | 3,3,5-Trimethyl cyclohexyl-2-hydroxy benzoate; homosalate | 118-56-9 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate; Octocrylene | 6197-30-4 |
| 30 | 2-ethylhexyl 4-(dimethylamino)benzoate | 21245-02-3 |
| 32 | 2-ethylhexyl salicylate | 118-60-5 |
| 33 | Benzoic acid, 4,4',4''-(1,3,5-triazine-2,4,6-triyltriimino)tris-, tris(2-ethylhexyl)ester; 2,4,6-Trianilino-(p-carbo-2'-ethylhexyl-1'-oxi)-1,3,5-triazine; octyl triazone | 88122-99-0 |
| 34 | 4-aminobenzoic acid | 150-13-0 |
| 35 | Benzoic acid, 4-amino-, ethyl ester, polymer with oxirane | 113010-52-9 |
| 38 | 2-phenyl-1H-benzimidazole-5-sulphonic acid; phenylbenzimidazolsulfonic acid | 27503-81-7 |

TABLE 3-continued

Suitable UV filter substances and adjuvants which can be additionally used with the compounds of formula (1)

| No. | Chemical Name | CAS No. |
|---|---|---|
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid]; Cibafast H | 90457-82-2 |
| 42 | Titanium dioxide | 13463-67-7 |
| 44 | Zinc oxide | 1314-13-2 |
| 45 | 2,2'-Methylene-bis-[6-(2H-benzotriazol-2-yl)-4-(1,1,3,3-tetramethyl-butyl)-phenol]; Tinosorb M | 103597-45-1 |
| 46 | 2,4-bis{[4-(2-ethylhexyloxy)-2-hydroxy]-phenyl}-6-(4-methoxyphenyl)-(1,3,5)-triazine; Tinosorb S | 187393-00-6 |
| 47 | 1H-Benzimidazole-4,6-disulfonic acid, 2,2'-(1,4-phenylene)bis-, disodium salt | 180898-37-7 |
| 48 | Benzoic acid, 4,4'-[[6-[[4-[[(1,1-dimethylethyl)amino]carbonyl]phenyl]-amino]1,3,5-triazine-2,4-diyl]diimino]bis-, bis(2-ethylhexyl)ester; di-ethylhexyl butamido triazone; Uvasorb HEB | 154702-15-5 |
| 49 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | 155633-54-8 |
| 50 | Dimethicodiethylbenzalmalonate; Polysilicone 15; Parsol SLX | 207574-74-1 |
| 51 | Benzenesulfonic acid, 3-(2H-benzotriazol-2-yl)-4-hydroxy-5-(1-methylpropyl)-, monosodium salt; Tinogard HS | 92484-48-5 |
| 53 | 1-Dodecanaminium, N-[3-[[4-(dimethylamino)benzoyl]amino]propyl]-N,N-dimethyl-, salt with 4-methylbenzenesulfonic acid (1:1); Escalol HP610 | 156679-41-3 |
| 54 | 1-Propanaminium, N,N,N-trimethyl-3-[(1-oxo-3-phenyl-2-propenyl)-amino]-, chloride | 177190-98-6 |
| 55 | 1H-Benzimidazole-4,6-disulfonic acid, 2,2'-(1,4-phenylene)bis- | 170864-82-1 |
| 56 | 1,3,5-Triazine, 2,4,6-tris(4-methoxyphenyl)- | 7753-12-0 |
| 57 | 1,3,5-Triazine, 2,4,6-tris[4-[(2-ethylhexyl)oxy]phenyl]- | 208114-14-1 |
| 58 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 59 | 2-Propenoic acid, 3-(1H-imidazol-4-yl)- | 104-98-3 |
| 60 | Benzoic acid, 2-hydroxy-, [4-(1-methylethyl)phenyl]methyl ester | 94134-93-7 |
| 61 | 1,2,3-Propanetriol, 1-(4-aminobenzoate); glyceryl PABA | 136-44-7 |
| 62 | Benzeneacetic acid, 3,4-dimethoxy-α-oxo- | 4732-70-1 |
| 63 | 2-Propenoic acid, 2-cyano-3,3-diphenyl-, ethyl ester | 5232-99-5 |
| 64 | Anthralinic acid, p-menth-3-yl ester | 134-09-8 |
| 65 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |
| 66 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |
| 68 | sterols (cholesterol, lanosterol, phytosterols), as described in WO0341675 | |
| 69 | mycosporines and/or mycosporine-like amino acids as described in WO2002039974, e.g. Helioguard 365 from Milbelle AG, isolated mycosporine like amino acids from the red alga porphyra umbilicalis (INCI: Porphyra Umbilicalis) that are encapsulated into liposomes,) | |
| 70 | alpha-lipoic-acid as described in DE 10229995 | |
| 71 | synthetic organic polymers as described in EP 1371358, [0033]-[0041] | |
| 72 | phyllosilicates as described in EP 1371357 [0034]-[0037] | |
| 73 | silica compounds as described in EP1371356, [0033]-[0041] | |
| 74 | inorganic particles as described in DE10138496 [0043]-[0055] | |
| 75 | latex particles as described in DE10138496 [0027]-[0040] | |
| 76 | 1H-Benzimidazole-4,6-disulfonic acid, 2,2'-(1,4-phenylene)bis-, disodium salt; Bisimidazylate; Neo Heliopan APC | 180898-37-7 |
| 77 | Pentanenitrile, 2-[2,3-dihydro-5-methoxy-3,3-dimethyl-6-[(2-methyl-2-propenyl)oxy]-1H-inden-1-ylidene]-4,4-dimethyl-3-oxo- | 425371-15-9 |
| 78 | Pentanenitrile, 2-(2,3-dihydro-6-hydroxy-5-methoxy-3,3-dimethyl-1H-inden-1-ylidene)-4,4-dimethyl-3-oxo- | 425371-14-8 |
| 79 | Benzenepropanenitrile, α-(2,3-dihydro-3,3,5-trimethyl-1H-inden-1-ylidene)-β-oxo- | 425371-11-5 |
| 80 | Cyclohexanepropanenitrile, α-[5-(1,1-dimethylethyl)-2,3-dihydro-3,3-dimethyl-1H-inden-1-ylidene]-1-methyl-β-oxo- | 425371-10-4 |
| 81 | Pentanenitrile, 2-[6-(acetyloxy)-2,3-dihydro-5-methoxy-3,3-dimethyl-1H-inden-1-ylidene]-4,4-dimethyl-3-oxo- | 425371-09-1 |
| 82 | Pentanenitrile, 2-[2,3-dihydro-5-methoxy-3,3-dimethyl-6-[2-methyl-3-[1,3,3,3-tetramethyl-1-[(trimethylsilyl)oxy]disiloxanyl]propoxy]-1H-inden-1-ylidene]-4,4-dimethyl-3-oxo- | 425371-08-0 |
| 83 | Pentanenitrile, 2-(2,3-dihydro-5-methoxy-3,3,6-trimethyl-1H-inden-1-ylidene)-4,4-dimethyl-3-oxo- | 425371-07-9 |
| 84 | Pentanenitrile, 4,4-dimethyl-3-oxo-2-(2,3,7,8-tetrahydro-8,8-dimethyl-6H-indeno[5,6-b]-1,4-dioxin-6-ylidene)- | 425371-06-8 |

TABLE 3-continued

Suitable UV filter substances and adjuvants which can be additionally used with the compounds of formula (1)

| No. | Chemical Name | CAS No. |
|---|---|---|
| 85 | Pentanenitrile, 2-(2,3-dihydro-3,3,6-trimethyl-1H-inden-1-ylidene)-4,4-dimethyl-3-oxo- | 425371-05-7 |
| 86 | Pentanenitrile, 2-(2,3-dihydro-3,3,5,6-tetramethyl-1H-inden-1-ylidene)-4,4-dimethyl-3-oxo- | 425371-04-6 |
| 87 | Pentanenitrile, 2-(2,3-dihydro-5-methoxy-3,3,4,6-tetramethyl-1H-inden-1-ylidene)-4,4-dimethyl-3-oxo- | 425371-03-5 |
| 88 | Pentanenitrile, 2-(2,3-dihydro-5,6-dimethoxy-3,3-dimethyl-1H-inden-1-ylidene)-4,4-dimethyl-3-oxo- | 261356-13-2 |

The benzotropolone derivatives of formula (1) may also be used in admixture with phenolic or lactone-type antioxidants as disclosed for example in WO00/25731.

The benzotropolone derivatives of formula (1) may also be used in admixture with hindered amine light stabilizers as disclosed in WO 03/103622, e.g., hindered nitroxyl, hydroxylamine and hydroxylamine salt compounds.

In order to optimize the anti-oxidizing effect, the household and/or personal care application could contain at least one further hydrophilic or lipophilic antioxidant within the concentration range from 0.0001% to 10% of the total weight of the preparation. Those additional antioxidants are preferably selected from the group containing:

- tocopherol (α, β, γ, δ isomers, in particular vitamin E) and its derivatives (in particular vitamin E derivatives such as vitamin E acetate, vitamin E linoleate, vitamin E nicotinate and vitamin E succinate)
- tocotrienol (α, β, γ, δ isomers), containing one unsaturated fatty chain, and its esters of acids
- ascorbic acid and its esters of acids such as phosphoric acid and also sodium, potassium, lithium and magnesium salts, Ascorbyl Tetraisopalmitate, further ester with pyrrolidoncarboxylic acid and esters of acids with general formulas

$$H(CH_2)_n(CHR)COOH \quad (3)$$

and

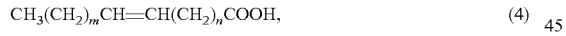

$$CH_3(CH_2)_m CH=CH(CH_2)_n COOH, \quad (4)$$

wherein R is hydrogen atom or OH group, m, n are integral numbers from 0 to 20 where m+n sum is maximally 21.

Retinoids include all natural and/or synthetic analogs of vitamin A or retinal-like compounds which possess the biological activity of vitamin A in the skin as well as the geometric isomers and stereoisomers of these compounds. Preferred compounds are retinol, retinol esters (e.g., $C_2$-$C_{22}$ alkyl esters (saturated or unsaturated alkyl chains) of retinal, including retinyl palmitate, retinyl acetate, retinyl propionate), retinal, and/or retinoic acid (including all trans retinoic acid and/or 13-cis-retinoic acid) or derivatives. Other retinoids which are useful herein are described in U.S. Pat. No. 4,677,120, issued Jun. 30, 1987 to Parish et al; U.S. Pat. No. 4,885,311, issued Dec. 5, 1989 to Parish et al; U.S. Pat. No. 5,049,584, issued Sep. 17, 1991 to Purcell et al., U.S. Pat. No. 5,124,356, issued Jun. 23, 1992 to Purcell et al. Other suitable retinoids are tocopheryl-retinoate [tocopherol ester of retinoic acid (trans or cis)], adapalene [6-(3-(1-adamantyl)-4-methoxyphenyl)-2-naphtoic acid] and tazarotene (ethyl 6-[2-(4,4-dimethylthiochroman-6-yl)-ethynyl]nicotinate)

- carotenoids such as α-, β-, γ-, and δ-carotene, lutein, xanthophylls, zeaxanthine, violaxanthine, cryptoxanthine, fukoxanthine, antheraxanthine, lycopene, didehydrolycopene and tetradehydrolycopene carotenoids
- Lipoic acid and its derivatives such as alpha-lipoic acid
- Rutinic acid and its derivatives such as α-glucosylrutin, a water soluble flavonoid, rutin hydrate (vitamin P)
- Botanical extracts such as white and green tea extracts, black tea extracts, chicory leaf extract (*Cichorium intubybus*), Passionflower extract (*Passiflora incarnata*), *Aspalathus linearis* extract, rosemary extract, red leaf extract of Aceraceae Maple tree or of Rosaceae Cherry tree, *Curcuma longa* L (curcuminoids active ingredients), *Leontopodium alpinum* extract, *Emblica officinalis* (phyllanthus emblica) tree extract . . . .
- Phenolic acids such as caffeic acid, 3,4-dihydroxyphenyl acetic acid, 3,4-dihydroxybenzoic acid.
- Gallates such as gallic acid, methyl gallate, ethyl gallate, propyl gallate, octyl gallate, dodecyl gallate, amyl gallate, isoamyl gallate, acylated gallates like 3,4,5-tris(acetyloxy)benzoic acid methyl ester, 3,4,5-tris(acetyloxy)-benzoic acid propyl ester, 3,4,5-tris(acetyloxy)-benzoic acid octyl ester.
- Catechols such as 1,2-dihydroxybenzene, 3-methylcatechol, 4-tert-butyl catechol or such as acylated catechols like catechol diacetate, 3-methylcatechol diacetate, catechol acetate.
- Pyrogallols such as 1,2,3-trihydroxybenzene, 4-ethyl pyrogallol, 4-propyl pyrogallol, 4-butyl pyrogallol, 4-amyl pyrogallol, 4-isoamyl pyrogallol, 4-octyl pyrogallol, 4-dodecyl pyrogallol or such as acylated pyrogallols like pyrogallol acetate, pyrogallol diacetate, pyrogallol triacetate.
- Flavonoids and polyphenols such as flavanones selected from the group consisting of unsubstituted flavanones, mono-substituted flavanones and mixtures thereof; chalcones selected from the group consisting of unsubstituted Chalcones, mono-substituted chalcones, di-substituted chalcones, tri-substituted chalcones, and mixtures thereof; flavones selected from the group consisting of unsubstituted flavones, mono-substituted flavones, di-substituted flavones, and mixtures thereof; one or more isoflavones; coumarins selected from the group consisting of unsubstituted coumarins, mono-substituted coumarins, di-substituted coumarins, and mixtures thereof; flavonols, anthocyanins, catechins such as green tea catechins like (−)-epigallocatechin-3-gallate, (−)-epicatechin, (−)-epigallocatechin and mixtures thereof, theaflavin, proanthocyanidins (Grape seed extract). Flavonoids which are broadly disclosed in U.S. Pat. Nos. 5,686,082 and 5,686,367 can also be used.
- chlorogenic acid and ferulic acid and their derivatives.

Tropolone derivatives such as tropolone (CAS No. 533-75-5) itself, hinokitiol, nootkatin, stipitatic acid, puberulic acid, stipitatonic acid, puberulonic acid, gamma-thujaplicin, beta-thujaplicin, colchiceine or tropolone derivatives as described in patent application WO 2008/003529 A1 and mixtures thereof.

It is also possible to use a third kind of antioxidants that interrupt the photochemical reaction chain triggered when UV radiation penetrates the skin or hair. Typical examples of such antioxidants are amino acids and their derivatives (e.g. glycine, histidine, acetyl histidine, tyrosine, caproyl tyrosine, tryptophan), imidazoles (e.g. urocanic acid) and derivatives thereof, peptides, such as D,L-carnosine, D-carnosine, L-carnosine and derivatives thereof (e.g. anserine), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine).

But also (metal) chelating agents (in particular α-hydroxy fatty acids, palmitic acid, phytin acid, lactoferrin) and preferably those disclosed in U.S. Pat. No. 5,487,884, issued Jan. 30, 1996 to Bisset et al; International publications No 91/16035 & No 91/16034 from Bush et al., published Oct. 31, 1995. Hydroxy acids (e.g. citric acid, lactic acid, malic acid, hydroxyl succinic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, coniferyl benzoate of benzoin resin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, N-[3-(3,5-di-tert-butyl-4-hydroxyphenyl)propionyl]-sulfanilic acid (and salts thereof, for example the disodium salts), zinc and derivatives thereof (e.g. ZnO, $ZnSO_4$), selenium and derivatives thereof (e.g. seleno methionine), stilbene and derivatives thereof (in particular hydroxystilbenes, resveratrol and pinosylvin) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned.

Further synthetic and natural antioxidants are listed e.g. in patent WO 0025731: Structures 1-3 (page 2), structure 4 (page 6), structures 5-6 (page 7) and compounds 7-33 (page 8-14).

Examples of suitable antioxidants include but are not limited to p-hydroxybenzoic acid and its derivatives (ethylisobutyl, glyceryl esters of p-hydroxybenzoic acid), salicylates (octylamyl, phenyl, benzyl menthyl, glycerol and dipropyleneglycol esters), benzylidene malonates, phenylmethyl propanoic acid derivatives like [(4-hydroxy-3,5-dimethoxyphenyl)methyl]-propanedioic acid, bis(2-ethylhexyl) ester (CAS No. 872182-46-2), hydroxyl or methoxy substituted benzophenones, uric or tannic acid and its derivatives.

Further additional antioxidants which can be used in the cosmetic compositions according to the present invention are chosen from the group consisting of acetylcysteine, 3-tert-butyl-4-hydroxyanisole, 2,6-di-tert-butyl-p-cresol, caffeic acid, chlorogenic acid, decylmercaptomethylimidazole, diacetyl thiodipropionate, digalloyl trioleate, dilauryl thiodipropionate, dimyristyl thiodipropionate, dioleyl tocopheryl methylsilanol, disodium rutinyl disulphate, distearyl thiodipropionate, ditridecyl thiodipropionate, dodecyl gallate, erythorbic acid, ethyl ferulate, hydroquinone and alkylated hydroquinones (e.g. tert-butylhydroquinone, diamylhydroquinone, di-tert-butylhydroquinone), p-hydroxyanisole, hydroxylamine hydrochloride, hydroxylamine sulphate, isooctyl thioglycolate, kojic acid, madecassicoside, methoxy-PEG-7-rutinyl succinate, octyl gallate, phenylthioglycolic acid, phloroglucinol, propyl gallate, rosmarinic acid and its derivatives, rutin, sodium erythorbate, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocophersolan, o-tolylbiguanide, tris(nonylphenyl) phosphite, dexpanthenol, alpha-hydroxy-carboxylic acids (in particular glycolic acid, lactic acid, mandelic acid) and salts thereof, di-methyloldimethylhydantoin, N-acylamino acids and salts thereof (in particular N-octanoylglycine) and hinokitol, and mixtures thereof for the long-term stabilization of a glycerol monoalkyl ether of the general formula

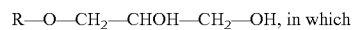

$R-O-CH_2-CHOH-CH_2-OH$, in which

R is a branched or unbranched $C_3$-$C_{18}$alkyl group, where the alkyl group can be substituted by one or more hydroxyl and/or $C_1$-$C_4$alkoxy group(s) and/or the alkyl chain can be interrupted by up to four oxygen atoms.

Further additional antioxidants which can be used in the cosmetic compositions according to the present invention are chosen from the group consisting of as well as alanine diacetic acid, quercetin, morin, 3,4-dihydroxybenzoic acid, thymol, carvacrol, catechins, as well as derivatives of gum benzoin resin, rutin and its derivatives, and benzylphosphonates such as, for example, dimethyl 2,5-di-tert-butyl-4-hydroxybenzylphosphonate, diethyl 3,5-di-tert-butyl-4-hydroxybenzylphosphonate and the calcium salt of monoethyl 3,5-di-tert-butyl-4-hydroxybenzylphosphonate.

Preferably the benzotropolone derivatives according to this invention are used in mixtures containing at least one further antioxidant selected from a gallate derivative, catechol derivative or pyrogallol derivative.

Beside the benzotropolone derivatives of formula (1) the household and/or personal care compositions according to the present invention may also contain phenolic or lactone-type antioxidants as disclosed for example in WO00/25731 and/or hindered amine light stabilizers as disclosed in WO 03/103622, e.g. hindered nitroxyl, hydroxylamine and hydroxylamine salt compounds.

Personal Care Uses

The benzotropolone derivatives of formula (1) may be used as single component or in mixture with other stabilizers in particular for skin-care products, bath and shower additives, preparations containing fragrances and odoriferous substances, hair-care products, dentifrices, deodorizing and antiperspirant preparations, decorative preparations, light protection formulations and preparations containing active ingredients.

Skin-care products are, in particular, body oils, body lotions, body gels, treatment creams, skin protection ointments, shaving preparations, such as shaving foams or gels, skin powders, such as baby powder, moisturizing gels, moisturizing sprays, revitalizing body sprays, cellulite gels and peeling preparations.

Suitable bath and shower additives are shower gels, bath-salts, bubble baths and soaps.

Preparations containing fragrances and odoriferous substances are in particular scents, perfumes, toilet waters and shaving lotions (aftershave preparations).

Suitable hair-care products are, for example, shampoos for humans and animals, in particular dogs, hair conditioners, products for styling and treating hair, perming agents, hair sprays and lacquers, hair gels, hair fixatives and hair dyeing or bleaching agents.

Suitable dentifrices are in particular tooth creams, toothpastes, mouth-washes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The mentioned body-care products may be in the form of creams, ointments, pastes, foams, gels, lotions, powders, make-ups, sprays, sticks or aerosols.

They preferably contain the benzotropolone derivatives of formulae (1) and, optionally, other UV absorbers, sterically hindered amines, complexing agents and phenolic or non-phenolic antioxidants.

The present invention therefore also relates to a body-care product comprising at least one benzotropolone derivative of formula (1).

The benzotropolone derivatives of formula (1) are present in the body care and household products in a concentration of about 5 to about 10000 ppm, based on the total formulation, preferably from about 10 to about 5000 ppm, and most preferably from about 100 to about 1000 ppm.

The cosmetic compositions according to the present invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of C12-C15 alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$-carboxylic acids with linear C6-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctylstearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Natural or Synthetic Triglycerides Including Glyceryl Esters and Derivatives

Di- or tri-glycerides, based on C6-C18 fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes

Ikylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially (aurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carbocyclic acids and their salts: alkaline soap of sodium, potassium and ammonium, metallic soap of calcium or magnesium, organic basis soap such as Lauric, palmitic, stearic and oleic acid etc. Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkyl-phenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan, glucose derivatives, $C_8$-$C_{22}$ alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, amonium and ethanolamine lauryl sulfates, lauyl ether sulfates, sodium laureth sulfates, sulfosuccinates, aceyl isothionates, alkanolamide sulfates, taurines, methyl taurines, imidazole sulfates. Amine derivatives, amine salts, ethoxylated amines, oxide amine with chains containing an heterocycle such as alkyl imidazolines, pyridine derivatives, isoquinoteines, cetyl pyridinium chlorure, cetyl pyridinium bromide, quaternary ammonium such as cetyltrimethylbroide amonium broide (CTBA), stearylalkonium. Amide derivatives, alkanolamides such as acylamide DEA, ethoxylated amides such as PEG-n acylamide, oxydeamide. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block(oxyethylene).

Zwitterionic surfactants that carry at least one quaternary ammonium group and at least one carboxylate and/or sulfonate group in the molecule. Zwitterionic surfactants that are especially suitable are betaines, such as N-alkyl-N,N dimethylammonium glycinates, cocoalkyldimethylammonium glycinate, N-acylaminopropyl-N,N-dimethylammonium glycinates, cocoacylaminopropyldimethylammonium glycinate and 2 alkyl-3-carboxymethyl-3-hydroxyethylimidazolines each having from 8 to 18 carbon atoms in the alkyl or acyl group and also cocoacylaminoethylhydroxy-ethylcarboxymethylglycinate, N-alkylbetaine, N-alkylaminobetaines. Alkylimidazolines, alkylopeptides, lipoaminoacides, self emulsifying bases and the compounds as described in K. F. DePolo, A short textbook of cosmetology, Chapter 8, Table 8-7, p 250-251.

Non ionic emulsifiers such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20[Polawax GP 200, Polawax NF], cetearyl alcohol and cetearyl polyglucoside [Emulgade PL 1618], cetearyl alcohol and cetaearth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Super-Fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, monoand/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers silicon dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropylmethylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80(steareth-10 alkyl ether/acrylates copolymer), Salcare SC81(acrylates copolymer), Salcare SC91 and Salcare AST (sodium acrylates copolymer/PPG-1 trideceth-6), sepigel 305(polyacrylamide/laureth-7), Simulgel NS and Simulgel EG (hydroxyethyl acrylate/sodium acryloyldimethyl taurate copolymer), Stabilen 30 (acrylates/vinyl isodecanoate crosspolymer), Pemulen TR-1 (acrylates/C10-30 alkyl acrylate crosspolymer), Luvigel EM (sodium acrylates copolymer), Aculyn 28 (acrylates/beheneth-25 methacrylate copolymer), etc.

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylamides, quaternised vinylpyrrolidone/vinyl imidazole polymers, for example Luviquatâ (BASF), condensation products of polyglycols and amines, quaternised collagen polypeptides, for example lauryldimonium hydroxypropyl hydrolyzed collagen (LamequatâL/Grünau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinyl-pyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylatetert. butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Cationic Surfactants cetyl trimethyl ammonium bromide (CTAB), dimethicone copolyols, amidomethicones, acrylamidopropyltrimonium chloride/Acrylamide copolymer, guar hydroxypropyl trimonium chloride, hydroxycetyl hydroxyethyl dimonium chloride quaternium compounds as listed in International Cosmetic Ingredient Dictionary and Handbook, 7$^{th}$ Edition 1997, for example Quaternium-80, polyquaternium compounds, as listed in International Cosmetic Ingredient Dictionary and Handbook, 7$^{th}$ Edition 1997, for example polyquaternium-5, polyquaternium-6, polyquaternium-7, polyquaternium-10, polyquaternium-11, polyquaternium-17, polyquaternium-18, polyquaternium-24 or polyquaternium-27, polyquaternium-28, polyquaternium-32, polyquaternium-37.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients are for example, antiperspirants, for example aluminium chlorohydrates (see J. Soc. Cosm. Chem. 24, 281 (1973)). Under the trade mark Locrona of Hoechst AG, Frankfurt (FRG), there is available commercially, for example, an aluminium chlorohydrate corresponding to formula $Al_2(OH)_5Cl \times 2.5H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2,4-dichlorophenoxy)phenol (Triclosan, Irgasan, BASF) has also proved especially effective.

Anti-Dandruff Agents

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Hydrotropic Agents

For improvement of the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols for that purpose comprise preferably 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives

Suitable preservatives include, for example methyl-, ethyl-, propyl-, butyl-parabens, benzalkonium chloride, 2-bromo-2-nitro-propane-1,3-diol, dehydroacetic acid, diazolidinyl urea, 2-dichloro-benzyl alcohol, dmdm hydantoin, formaldehyde solution, methyldibromoglutanitrile, phenoxyethanol, sodium hydroxymethylglycinate, imidazolidinyl urea, triclosan and further substance classes listed in the following reference: K. F. Depolo—A Short Textbook Of Cosmetology, Chapter 7, Table 7-2, 7-3, 7-4 And 7-5, P210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

Mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent.

Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Other Adjuvants

It is furthermore possible for the cosmetic preparations to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, propellants, such as propane/butane mixtures, N2O, dimethyl ether, CO2, N2 or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

The present stabilizer systems are particularly suitable for stabilizing body care products, in particular:
- skin-care preparations, e.g. skin-washing and cleansing preparations in the form of tablet-form or liquid soaps, soapless detergents or washing pastes,
- bath preparations, e.g. liquid (foam baths, milks, shower preparations) or solid bath preparations, e.g. bath cubes and bath salts;
- skin-care preparations, e.g. skin emulsions, multi-emulsions or skin oils; body oils, body lotions, body gels; skin protection ointments;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances and odoriferous substances containing preparations (scents, eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile;

dentifrices, in particular tooth creams, toothpastes, mouthwashes, mouth rinses, anti-plaque preparations and cleaning agents for dentures;

decorative preparations, in particular lipsticks, nail varnishes, eye shadows, mascaras, dry and moist make-up, rouge, powders, depilatory agents and suntan lotions cosmetic formulations containing active ingredients, in particular hormone preparations, vitamin preparations, vegetable extract preparations and antibacterial preparations.

Suitable cosmetic formulations containing active ingredients are in particular hormone preparations, vitamin preparations, vegetable extract preparations and antibacterial preparations.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a stick, in the form of a spray (spray with propellent gas or pump-action spray) or an aerosol, in the form of a foam, or in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition:

0.01 to 5% by weight of the compound of formula (1), 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

a1) spontaneously emulsifying stock formulation, comprising the compound of formula (1) according to the invention, optionally another stabilizer, PEG-6-C10oxoalcohol and sorbitan sesquioleate, to which water and any desired quaternary ammonium compound, for example 4% minkamidopropyl dimethyl-2-hydroxyethylammonium chloride or Quaternium 80 is added;

a2) spontaneously emulsifying stock formulation comprising the compound of formula (1) according to the invention, optionally another stabilizer, tributyl citrate and PEG-20-sorbitan monooleate, to which water and any desired quaternary ammonium compound, for example 4% minkamidopropyl dimethyl-2-hydroxyethylammonium chloride or Quaternium 80 is added;

b) quat-doped solutions comprising the compound of formula (1) according to the invention in butyl triglycol and tributyl citrate; and optionally another stabilizer;

c) mixtures or solutions comprising the compound of formula (1) according to the invention with alkylpyrrolidone; and optionally another stabilizer.

Examples of body care products of the present invention are listed in the Table below:

| Body care product | Ingredients |
|---|---|
| moisturising cream | vegetable oil, emulsifier, thickener, perfume, water, antioxidant, UV absorbers |
| shampoo | surfactant, emulsifier, preservatives, perfume, antioxidant, UV absorbers |
| Toothpaste | cleaning agent, thickener, sweetener, flavor, colorant, antioxidant, water, UV absorbers |
| lip-care stick | vegetable oil, wax, $TiO_2$, antioxidant, UV absorbers |

Household Products

The stabilizer systems of the present invention are also used in household cleaning and treatment agents, for example in laundry products and fabric softeners, liquid cleansing and scouring agents, glass detergents, neutral cleaners (all-purpose cleaners), acid household cleaners (bath), bathroom cleaners, WC cleaners, for instance in washing, rinsing and dishwashing agents, kitchen and oven cleaners, clear rinsing agents, dishwasher detergents, shoe polishes, polishing waxes, floor detergents and polishes, metal, glass and ceramic cleaners, textile-care products, rug cleaners and carpet shampoos, agents for removing rust, color and stains (stain remover salt), furniture and multipurpose polishes and leather and vinyl dressing agents (leather and vinyl sprays) and air fresheners.

Household cleaning agents are aqueous or alcoholic (ethanol or isopropyl alcohol) solutions of one or more of the following components:
  anionic, nonionic, amphoteric and/or cationic surfactants
  soaps, prepared by saponification of animal and vegetable greases
  inorganic acids, like hydrochloric acid, phosphoric acid, or sulfuric acid,
  for basic products inorganic (NaOH or KOH) or organic bases;
  abrasives for improved cleaning of surfaces,
  waxes and/or silicones for maintenance and protection of surfaces,
  polyphosphates,
  substances which release hypochlorite or halogens;
  peroxides comprising bleaching activators like TAED, for example sodium perborate or $H_2O_2$;
  enzymes;
  in washing detergents discoloration inhibitors, soil-release compounds, grey scale inhibitors, foam inhibitors, fluorescent whitening agents;
  cleaning agents based on wax may comprise solvents selected from benzine, turpentine and/or paraffines and emulsifiers based on wax;
  filling agents like silicates, polyphosphates, Zeolithes for powdery cleaning agents;
  pigments, lakes or soluble dyes;
  perfumes; and
  light stabilizers, antioxidants and chelating agents.
  Colored cleaning agents and decorative cosmetic products can comprise the following dyes:
  inorganic pigments, for example iron oxide (Iron Oxide Red, Iron Oxide Yellow, Iron Oxide Black, etc.), Ultramarines, Chromium Oxide Green or Carbon Black;
  natural or synthetic organic pigments;
  disperse dyes which may be solubilzed in solvents like direct hair dyes of the HC type, for example HC Red No. 3, HC Blue No. 2 and all other hair dyes listed in International Cosmetic Ingredient Dictionary and Handbook, 7th edition 19997) or the dispersion dyes listed in Color Index International or Society of Dyers and Colourists;
  color varnishes (insoluble salts of soluble dyes, like many Ca-, Ba- or Al-salts of anionic dyes);
  soluble anionic or cationic dyes, like acid dyes (anionic), basic dyes (cationic), direct dyes, reactive dyes or solvent dyes.

Generally, for the coloration of household- and body care products all substances are suitable which have an absorption in the visible light of electromagnetic radiation (wave length of ca. 4000 to 700 nm). The absorption is often caused by the following chromophores:

Azo- (mono-, di, tris-, or poly-)stilbene-, carotenoide-, diarylmethan-, triarylmethan-, xanthen-, acridin-, quinoline, methin- (also polymethin-), thiazol-, indamin-, indophenol-, azin-, oxazin, thiazin-, anthraquinone-, indigoid-, phtalocyanine- and further synthetic, natural and/or inorganic chromophores.

The present invention also relates to home care and fabric care products such as drain cleaners, disinfectant solutions, upholstery cleaners, automotive care products (e.g., to clean and/or polish and protect paint, tires, chrome, vinyl, leather, fabric, rubber, plastic and fabric), degreasers, polishes (glass, wood, leather, plastic, marble, granite, and tile, etc.), and metal polishes and cleaners. Antioxidants are suitable to protect fragrances in above products as well as in dryer sheets. The present invention also relates to home care products such as candles, gel candles, air fresheners and fragrance oils (for the home).

Typical examples of household cleaning and treating agents are listed in the table below:

| Household cleaners/ household treating agents | Ingredients |
|---|---|
| detergent concentrate | surfactant mixture, ethanol, antioxidant, water, UV absorbers, antioxidants |
| shoe polishwax | wax emulsifier, antioxidant, water, preservative, UV absorbers, antioxidants |
| wax-containing floor cleaning agent | emulsifier, wax, sodium chloride, light stabiliser of formulae (1) and (2), water, preservative UV absorbers, antioxidant |

The benzotropolone derivatives of formula (1) according to the present invention are for example incorporated by dissolution in an oil phase or alcoholic or water phase, where required at elevated temperature.

The present body care products and household products have high stability towards color changes and chemical degradation of the ingredients present in these products. For example, present compositions that comprise a dye are found to have excellent color stability.

The following Examples illustrate the invention.

In the following Examples the stabilizers listed in the Table below have been used:

| Comp. of formula | Structure |
|---|---|
| (B-1) | 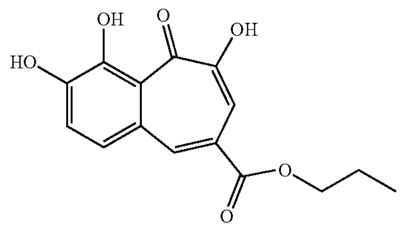 [SMILES: CCCOC(=O)c1cc(O)c(=O)c2c(O)c(O)ccc2c1] |
| (B-2) | 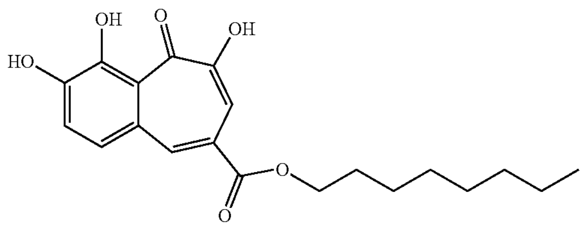 [SMILES: CCCCCCCCOC(=O)c1cc(O)c(=O)c2c(O)c(O)ccc2c1] |
| (B-32) | 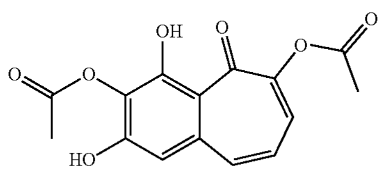 [SMILES: CC(=O)Oc1c(O)cc2cccc(OC(C)=O)c(=O)c2c1O] |
| (B-37) | 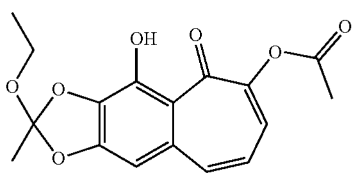 [SMILES: CCOC1(C)Oc2cc3cccc(OC(C)=O)c(=O)c3c(O)c2O1] |
| (B-18) | 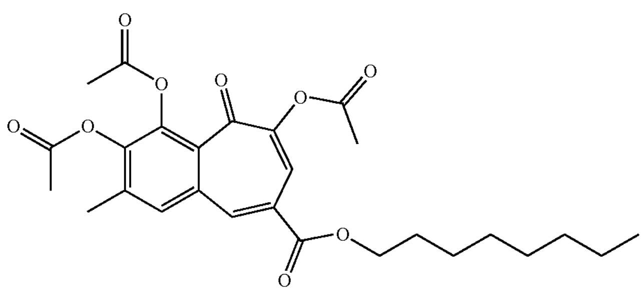 [SMILES: CCCCCCCCOC(=O)c1cc(OC(C)=O)c(=O)c2c(OC(C)=O)c(OC(C)=O)c(C)cc2c1] |
| (B-44) | 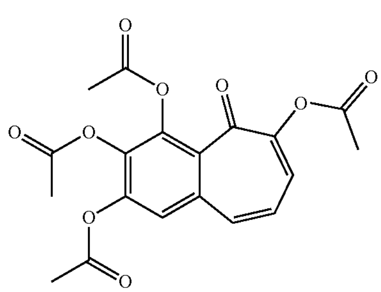 [SMILES: CC(=O)Oc1cc2cccc(OC(C)=O)c(=O)c2c(OC(C)=O)c1OC(C)=O] |
| (BTE) | Black tea extract (methanolic extract of Darjeeling tea) |
| AO 01 | 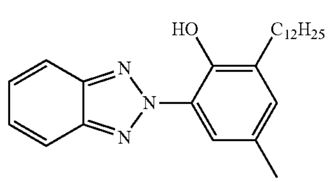 |

-continued
| Comp. of formula | Structure |
|---|---|
| AO 02 | 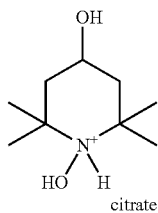 citrate |
| AO 03 | 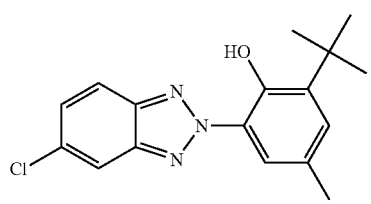 [SMILES: Cc1cc(-n2nc3ccc(Cl)cc3n2)c(O)c(C(C)(C)C)c1] |
| AO 04 | 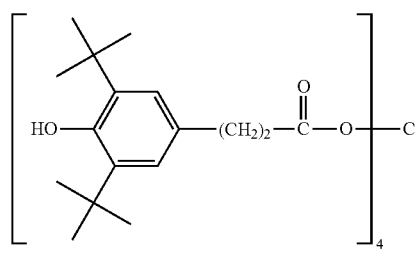 |
| AO 05 | 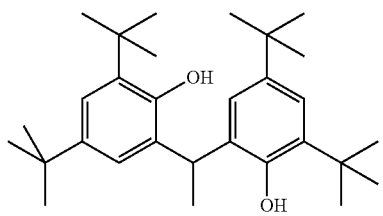 [SMILES: CC(c1cc(C(C)(C)C)cc(C(C)(C)C)c1O)c1cc(C(C)(C)C)cc(C(C)(C)C)c1O] |
| AO 06 | 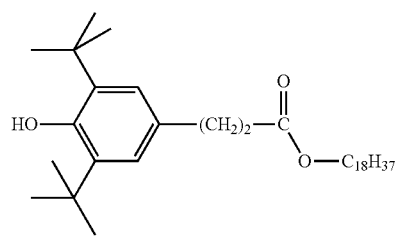 |
| AO 07 | 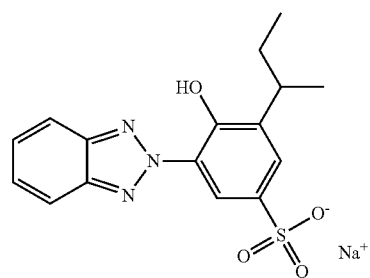 [SMILES: CCC(C)c1cc(S(=O)(=O)[O-])cc(-n2nc3ccccc3n2)c1O ; [Na+]] |

| Comp. of formula | Structure |
|---|---|
| AO 08 | 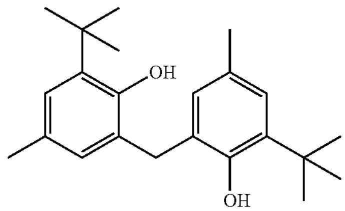 [SMILES: Cc1cc(Cc2cc(C)cc(C(C)(C)C)c2O)c(O)c(C(C)(C)C)c1] |
| AO 09 | 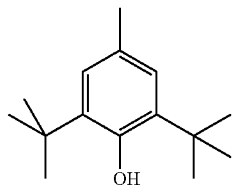 [SMILES: Cc1cc(C(C)(C)C)c(O)c(C(C)(C)C)c1] |

Efficacy Comparison to State-of-the Art Stabilizers

EXAMPLE 1

The following colored basic shampoo formulation is prepared:

| Sodium Laureth Ether Sulfate | 10% |
|---|---|
| Cocamidopropylbetaine | 3% |
| Citric Acid | to pH 5 |
| FD&C Blue No. 1 | 0.002% |
| Stabilizer | 0.01% |

The following stabilized and unstabilized samples of this formulation are prepared for light stability testing:
1. unstabilized basic shampoo formulation
2. basic shampoo formulation plus 0.01% of the compound of formula (B-1)
3. basic shampoo formulation plus 0.01% of the compound of formula (B-2)
4. basic shampoo formulation plus 0.01% of the compound of formula (B-32)
5. basic shampoo formulation plus 0.01% of the compound of formula (B-18)

The formulations were filled into 30 ml glass bottles and irradiated in an ATLAS Suntest XLS+Xenon Lamp (light intensity 500 W/m2, spectrum of light adjusted to indoor conditions, sample chamber temperature: 32° C.).

Results after 15 hours irradiation.

| Sample | Observation after irradiation |
|---|---|
| 1 | Faded/colorless |
| 2 | No change |
| 3 | No change |
| 4 | No change |
| 5 | No change |

Results after 30 hours irradiation.

| Sample | Observation after irradiation |
|---|---|
| 1 | Colorless |
| 2 | No change |
| 3 | No change |
| 4 | No change |
| 5 | faded |

All stabilizers increased the stability of the formulation significantly. Stabilizer of formula (B-18), according to current invention, showed additionally the benefit that it did not alter the initial color, which is of advantage if specific desired shades don't allow for yellowish colored components.

EXAMPLE 2

The following colored basic shampoo formulation is prepared:

| Sodium Laureth Ether Sulfate | 10% |
|---|---|
| Cocamidopropylbetaine | 3% |
| Citric Acid | to pH 5 |
| Dye | 0.002% |
| Stabilizer | 0.01% |

The formulation is colored with PURICOLOR Blue ABL9 (BASF, FD&C Blue No. 1, Acid Blue 9), and PURICOLOR Red ARE33 (BASF, D&C Red 33, Acid Red 33), respectively.

The following stabilized and unstabilized samples of this formulation are prepared for light stability testing:
1. unstabilized basic shampoo formulation
2. basic shampoo formulation plus 0.01% of the compound of formula (B-18)
3. basic shampoo formulation plus 0.01% of TINOGARD TL (BASF)

The formulations were filled into 30 ml glass bottles and irradiated in an ATLAS Suntest XLS+Xenon Lamp (light intensity 500 W/m2, spectrum of light adjusted to indoor conditions, sample chamber temperature: 32° C.).

Results for blue colored shampoo after 12 hours irradiation.

Results for blue colored shampoo after 25 hours irradiation.

| Sample | Observation after irradiation |
|---|---|
| 1 | Faded/colorless |
| 2 | No change |
| 3 | No change |

Results for red colored shampoo after 10 hours irradiation.

| Sample | Observation after irradiation |
|---|---|
| 1 | Faded/colorless |
| 2 | Very slightly lighter |
| 3 | Faded/colorless |

Results for red colored shampoo after 25 hours irradiation.

| Sample | Observation after irradiation |
|---|---|
| 1 | Faded/pale brown |
| 2 | No change |
| 3 | No change |

| Sample | Observation after irradiation |
|---|---|
| 1 | Faded/colorless |
| 2 | Very slightly lighter |
| 3 | Faded/colorless |

Compound of formula (B-18) performed significantly better than state-of-the-art broadbandUV absorbers like TINOGARD TL with both tested dyes.

EXAMPLE 3

The following stabilized and unstabilized samples were prepared for antioxidation testing:
1. pure castor oil
2. castor oil containing 0.1% of compound of formula (B-32)
3. castor oil containing 0.1% of the antioxidant TINOGARD TT (BASF)
4. castor oil containing 0.1% of the antioxidant BHT
5. castor oil containing 0.1% of Quercetin The samples were placed in a RACIMAT and heated to 140° C. An airflow of 15 L/min was adjusted. The airstream bubbles through each heated sample and afterwards through a water reservoir. Thus all volatile organic compounds formed by the oxidation process are carried into the water reservoir by the airstream. The conductivity of the water reservoir is monitored online during the measurement. Once oxidation starts volatile organic compounds like formic acid are transported into the water reservoir which results in a rapid (exponential) increase of conductivity. The time until oxidation starts is called "induction time".

The results are listed in the table below.

| Sample | Induction Time |
|---|---|
| 1 | 7.7 hours |
| 2 | 10.5 hours |
| 3 | 9.3 hours |
| 4 | 9.2 hours |
| 5 | 8.5 hours |

Sample 2, comprising a stabilizer according to the present invention, exhibits better oxidation stability compared to the state-of-the-art antioxidants like TINOGARD TT (Ciba) or BHT, and also performs significantly better than natural polyphenolic structures like Quercetin.

EXAMPLE 4-15

Preparation of Body-Care and Household Formulations

| Example 4: Preparation of a sprayable hair styling gel | | |
|---|---|---|
| Phase | Ingredients | (w/w) % |
| A | carbomer (1% dispersion) | 0.30 |
|   | water, demin. | 30.00 |
| B | glycerol | 2.00 |
|   | methylparaben | 0.20 |
| C | water, demin. | ad 100 |
|   | PVP/VA copolymer | 8.00 |
|   | triethanolamine (88%) | 0.12 |
|   | EDTA, disodium salt | 0.01 |
| D | light stabilizer of formula (B-18) | 0.01 |
|   | fragrance | 1.00 |

Preparation:

The components (A) are dispersed at room temperature.

(B) is mixed under heating until the paraben is completely dissolved and then (B) is added with gentle stirring to (A).

(C) is blended until it is completely dissolved and is slowly added under stirring to the mixture of (A) and (B).

(D) is blended until completely dissolved and is slowly added under stirring to the mixture of (A), (B) and (C).

The transparency of the gel can be increased by adding small amounts of triethanolamine (pH=5.6-5.75).

| Example 5: Preparation of a baby shampoo | |
|---|---|
| Ingredients | (w/w) % |
| cocoamidopropylbetaine | 35.00 |
| water, demin. | ad.100 |
| citric acid | q.s. (pH) |
| polyquaternium-15 | 0.15 |
| perfume oil | 0.30 |
| chlorophyll | 0.20 |
| light stabilizer of formula (B-2) | 0.02 |
| Compound of formula (AO 01) | 0.02 |
| colorant (D&C Yellow No. 5) | 0.02 |
| sodium chloride | 0.30 |

Preparation:

Surfactant and water are blended until a homogeneous solution is obtained. The pH is adjusted to 6.0-6.5 with citric acid. The other components are added, stabilizers are premixed with the fragrance oil. The mixture is stirred until it is completely dissolved.

Example 6: Preparation of a perfumed toilet water

| Ingredients | (w/w) % |
| --- | --- |
| ethanol, 96% | 60 |
| d-limonene | 5 |
| cedrene | 1.5 |
| citronellol | 0.5 |
| savin | 0.5 |
| stabilizer of formula (B-44) | 0.05 |
| light stabilizer of formala (AO 01) | 0.05 |
| light stabilizer of formula (AO 02) | 0.03 |
| Antioxidant of formula (AO 06) | 0.02 |
| S,S-EDDS | 0.01 |
| colorant (D&C Yellow No. 5) | 0.1 |
| water | ad. 100 |

Preparation:

The components are thoroughly mixed in the indicated sequence at 50° C. A clear homogeneous solution is obtained.

Example 7: Preparation of a lipstick, non-greasy

| Ingredients | (w/w) % |
| --- | --- |
| Carnauba wax | 2.5 |
| Beeswax, white | 20.0 |
| Ozekerite | 10.0 |
| Lanoline, anhydrous | 5.0 |
| Cetyl alcohol | 2.0 |
| Liquid paraffin | 3.0 |
| Isopropyl Myristate | 3.0 |
| Propylene glycol recinoleate | 4.0 |
| CI Pigment Red 4 | 9.0 |
| CI Pigment Blue 15 | 1.0 |
| Stabilizer of formula (B-32) | 0.05 |
| Castor Oil | ad 100 |

Example 8: Preparation of a lipstick, transfer resistant

| Ingredients | (w/w) % |
| --- | --- |
| Cyclomethicone | 41.50 |
| Isodecane | 10.00 |
| D&C Red No. 7 | 8.00 |
| Synthetic wax | 6.00 |
| Isostearyltrimethylpropane siloxysilicate | 5.00 |
| Cetylstearate/acetylated lanolin, 90:10 | 5.00 |
| Ceresin | 4.00 |
| Paraffin | 3.00 |
| Titanium dioxide | 2.00 |
| Methylparaben | 0.30 |
| Propylparaben | 0.10 |
| Antioxidant of formula (AO 04) | 0.10 |
| stabilizer of formula (B-1) | 0.10 |

Example 9: Preparation of a Rouge (powder)

| Ingredients | (w/w) % |
| --- | --- |
| Talcum | 56 |
| Zinc Stearate | 15 |
| Rice starch | 15 |
| Iron Oxide Red | 12 |
| Perfume | q.s. |
| stabilizer of formula (BTE) | 0.1 |

Example 10: Preparation of a Foundation cream

| Ingredients | (w/w) % |
| --- | --- |
| Titanium dioxide | 12.79 |
| Oleyl alcohol | 4.57 |
| Glyceryl stearate | 3.65 |
| Propylene glycol | 3.65 |
| Stearic acid | 1.83 |
| Magnesium aluminium silicate | 0.91 |
| Triethanolamine 99% | 0.91 |
| Iron Oxide Yellow | 0.64 |
| Iron Oxide Red | 0.32 |
| CI Pigment Brown 6 | 0.37 |
| Carboxymethyl cellulose | 0.10 |
| stabilizer of formula (B-44) | 0.10 |
| Water | ad 100 |

Example 11: Preparation of an Eyeliner

| Ingredients | (w/w) % |
| --- | --- |
| Polysaccharide resin (Kama KM 13, Kama) | 8.00 |
| Iron Oxide Black | 6.50 |
| Polysaccharide resin (Kama KM 13, Kama) | 8.00 |
| Carnauba wax | 1.00 |
| Triethanolamin, 99% | 1.00 |
| Hydrogenated polyisobutane | 1.00 |
| Hydrogenated polydecene | 1.00 |
| Sorbitan sesquioleate | 1.00 |
| Xanthum gum | 0.50 |
| Carboxymethyl cellulose | 0.40 |
| Magnesium aluminium silicate | 0.40 |
| Methyl paraben | 0.35 |
| Stearic acid | 2.50 |
| Lecithin | 0.20 |
| Imidazolidinyl urea | 0.10 |
| stabilizer of formula (B-32) | 0.10 |
| Antioxidant of formula (AO 05) | 0.05 |
| Water | to 100 |

Example 12: Preparation of an Eyelash Makeup

| Ingredients | (w/w) % |
| --- | --- |
| Paraffin Wax | 10.00 |
| Starch | 5.00 |
| Polyethylene | 5.00 |
| Iron Oxide Black | 7.00 |
| Carbomer (Carbopol, BFGoodrich) | 0.50 |
| Hydroxyethylcellulose | 0.50 |
| Panthenol | 2.00 |
| stabilizer of formula (B-2) | 0.05 |
| Water | ad 100 |

Example 13: Preparation of a Nail Varnish

| Ingredients | (w/w) % |
| --- | --- |
| Poly(1-trimethylsilylpropylene) | 0.30 |
| Nitrocellulose | 12.00 |
| Alkyd resin | 10.00 |
| Dibutyl phthalate | 4.00 |
| Camphor | 2.00 |
| Butyl acetate | 49.50 |
| Toluene | 20.00 |
| Pigment Red 57.1 | 1.00 |
| Quaternary bentonite | 1.00 |
| stabilizer of formula (B-18) | 0.20 |
| Light stabilizer of formula (AO 04) | 0.10 |

Preparation of Formulations of Household Products

Example 14: Preparation of a green-colored glass detergent:

| Ingredients | (w/w) % |
|---|---|
| anionic/amphoteric surfactants (Lumorol RK) | 0.7 |
| butyl glycol | 5.0 |
| isopropanol | 20.0 |
| d-limonene | 4.00 |
| colorant (D&C Green No. 2) | 0.05 |
| light stabilizer of formula (AO 02) | 0.05 |
| light stabilizer of formula (B-1) | 0.05 |
| water, demin. | ad. 100 |

Preparation:

The components are dissolved in the indicated sequence until a clear homogeneous mixture is obtained.

Example 15: Preparation of a floor wax

| Ingredients | (w/w) % |
|---|---|
| wax mixture | 12 |
| white spirit | ad 100 |
| d-limonene | 4.00 |
| light stabiliser of formula (B-18) | 0.10 |

Preparation:

The components are stirred in the indicated sequence until a homogeneous mixture is obtained.

SYNTHESIS EXAMPLE (1)

Preparation of B-20

1,7-dibutyl-2,3,4,6-tetrahydroxy-5H-Benzocyclohepten-5-one (CAS-No. 16492-78-7) (1.4 g) is dissolved in 40 ml of toluene and 0.8 ml triethyl orthoacetate and heated to 120° C. until ethanol evaporation ceases. The mixture is then evaporated to dryness and the residue lyophilized from dioxane after filtration from silicagel in order to remove dark impurities. The resulting yellow powder is soluble in hexane.

$^1$H-NMR (CDCl$_3$, 300 MHz): 9.00 (OH); 7.45 (d, 1H); 6.82 (d, 1H); 3.65 (dq, 1H); 3.53 (dq, 1H); 2.85 (t, 2H); 2.72 (t, 2H); 1.88 (s, 3H); 1.48-1.66 (m, 4H); 1.29-1.45 (m, 4H); 1.18 (t, 3H); 0.90 (dt, 6H).

$^{13}$C-NMR (CDCl$_3$, 75 MHz): 13.88; 13.95; 14.74; 22.51; 22.75; 24.80; 26.29; 31.23; 31.94; 34.11; 58.45; 112.85; 119.40; 127.11; 129.45; 129.52; 132.62; 133.91; 144.66; 150.61; 152.75; 181.76.

SYNTHESIS EXAMPLE (2)

Preparation of B-2

0.50 g of catechol (44.3 mmol, 98%) and 1.28 g of gallic acid octyl ester (44.3 mmol, 98%) are dissolved in 30 ml phthalate buffer (pH=5) and 10 mL ethyl acetate at room temperature. 3.0 mg (21.8 U/mg) of commercial (Sigma-Aldrich) laccase from *T. versicolor* are added and the mixture is stirred for 2 days at room temperature.

The organic phase is then separated and concentrated in vacuo to yield 1.02 g of crude compound B-2. After recrystallization from ethanol/water the desired product B-2 is yielded in 1.26 g as an dark orange powder. Melting point: 79° C. (decomposition).

$^1$H-NMR (DMSO, 300 MHz): 14.77 (s, 1H, OH), 10.00 (s, 2H, 20H); 8.27 (s, 1H); 7.612 (m, 2H); 7.48 (d, 1H); 4.28 (t, 2H); 1.73 (m, 2H); 1.16-1-42 (m, 10H); 0.85 (t, 3H).

SYNTHESIS EXAMPLE (3)

Preparation of B-1

6.74 g of catechol (60 mmol, 98%) and 8.66 g of gallic acid propyl ester (40 mmol, 98%) are dissolved in 400 mL phosphate buffer (pH=5) and 120 mL ethyl acetate at room temperature.

45.2 mg (21.8 U/mg) of commercial laccase from *T. versicolor* are added and the mixture is stirred for 4 days at room temperature.

The organic phase is then separated and concentrated in vacuo to yield 13.40 g of crude product. After recrystallization from water the desired product B-1 is yielded in 7.34 g as an orange powder. Melting point: 139° C.

$^1$H-NMR (DMSO, 300 MHz): 14.75 (s, 1H, OH), 10.15 (s, 1H, OH); 9.90 (s, 1H, OH); 8.26 (s, 1H); 7.61 (d, 1H); 7.60 (s, 1H); 7.48 (d, 1H); 4.25 (t, 2H); 1.76 (m, 2H), 0.99 (t, 3H).

SYNTHESIS EXAMPLE (4)

Preparation of B-32

To a solution of 3.00 g purpurogallin in 40 ml of pyridine 2.56 ml of acetic anhydride is added dropwise. After stirring for 1 h at 100° C. the mixture is evaporated to dryness and the orange residue is suspended in diethyl ether. The precipitate is filtrated off and dried in vacuum to yield 0.59 g of crude compound B-32. After boiling in diethyl ether/ethyl acetate (1:1) the desired product is obtained in 0.42 g as a yellow powder.

$^1$H-NMR (DMSO, 360 MHz): 15.29 (s, 1H); 11.38 (s, 1H); 7.57 (d, J=11.6, 1H); 7.35 (d, J=8.95, 1H); 6.99 (s, 1H); 6.78 (dd, 1H); 2.34 (s, 3H); 2.30 (s, 3H).

SYNTHESIS EXAMPLE (5)

Preparation of B-23

Purpurogallin (0.50 g) is dissolved in 20 ml of toluene and 0.43 ml triethyl orthoacetate and heated to 120° C. until ethanol evaporation ceases. The resulting orange suspension is then evaporated to dryness and the residue is stirred in dichloromethane. The precipitate is filtrated off and dried in the vacuum at 25° C. 450 mg of the desired product are isolated as an orange powder.

$^1$H-NMR (CDCl$_3$, 360 MHz): 14.61 (s, 1H); 8.56 (s, 1H); 7.34 (d, J=11.5, 1H); 7.19 (d, J=9.5, 1H); 6.86-6.80 (m, 2H); 3.72-3.59 (m, 2H); 1.92 (s, 3H); 1.24 (t, J=7.1, 3 H).

SYNTHESIS EXAMPLE (6)

Preparation of B-36

Compound B-37 is suspended in 10.0 ml of HCl$_{aq.}$ 0.1 solutions and stirred for 18 h at 25° C. The orange-yellow precipitate is filtrated off and dried in the vacuum. 0.318 g of the desired product are isolated as a beige powder.

$^1$H-NMR (DMSO, 360 MHz): 15.26 (s, 1H); 7.56 (d, 1H); 7.33 (d, 1H); 6.98 (s, 1H); 6.65 (dd, 1H); 2.30 (s, 3H).

SYNTHESIS EXAMPLE (7)

Preparation of B-37

To a solution of 0.636 g B-23 in 6.0 ml pyridine 0.207 ml of acetic anhydride are added at room temperature. The brown-orange solution is stirred for 1.5 h at room temperature and added to 30.0 ml of ice-water and stirred for 15 min at 0° C. The orange suspension is filtrated off and dried in the vacuum. 0.620 g of the desired product are isolated as an orange powder.

$^1$H-NMR (DMSO, 360 MHz): 14.78 (s, 1H); 7.68 (d, 1H); 7.43 (d, 1H); 7.26 (s, 1H); 6.82 (dd, 1H); 3.59-3.56 (m, 2H); 2.31 (s, 3H); 1.89 (s, 3H); 1.16 (t, 3H).

SYNTHESIS EXAMPLE (8)

Preparation of B-38

Compound B-1 (1.50 g) is dissolved in 35 ml of toluene and 1.89 ml triethyl orthoacetate and heated to 120° C. until ethanol evaporation ceases. The resulting orange suspension is then evaporated to dryness and the residue is stirred in 10.0 ml diethylether. The precipitate is filtrated off and dried in the vacuum at 25° C. 1.20 g of the desired product are isolated as a yellow powder.

$^1$H-NMR (CDCl$_3$, 360 MHz): 8.39 (s, 1H); 8.30 (s, 1H); 7.77 (s, 1H); 7.57 (d, 1H); 7.34 (d, 1H); 4.31 (t, 2H); 3.70-3.57 (m, 2H); 1.98 (s, 3H); 1.84-1.82 (m, 2H); 1.24 (t, 3H); 1.06 (t, 3H).

SYNTHESIS EXAMPLE (9)

Preparation of B-39

To a solution of 0.40 g B-23 in 4.0 ml pyridine 2.651 ml of acetic anhydride are added at room temperature. The brown mixture is stirred for 20 h at room temperature and added to 40.0 ml of ice-water and stirred for 15 min at 0° C. The beige suspension is filtrated off and the orange-yellow residue is dried in the vacuum. 0.198 g of the desired product are isolated as a yellow powder.

$^1$H-NMR (CDCl$_3$, 360 MHz): 7.14 (d, 1H); 6.92 (s, 1H); 6.78 (d, 1H); 6.52-6.47 (m, 1H); 3.703.54 (m, 2H); 2.35 (s, 3H); 2.29 (s, 3H); 1.87 (s, 3H); 1.21 (t, 3H).

SYNTHESIS EXAMPLE (10)

Preparation of B-5

Compound B-1 (0.35 g) is dissolved in 4.0 ml of pyridine at room temperature. 0.50 ml of acetic anhydride are added dropwise and the solution is stirred for 16 h at room temperature. Then the mixture is added to 5.0 ml of ice-water and stirred for 30 min at 15° C. The yellow precipitate is filtrated off, washed with water and dried in the vacuum at 30° C. 0.337 g of the desired product are isolated as a yellow powder.

$^1$H-NMR (DMSO, 360 MHz): 8.45 (s, 1H); 8.16 (d, 1H); 7.88 (d, 1H); 7.50 (s, 1H); 4.31 (t, 2H); 2.38 (s, 3H); 2.33 (s, 3H); 2.30 (s, 3H); 1.83-1.77 (m, 2H); 1.03 (t, 3H).

SYNTHESIS EXAMPLE (11)

Preparation of B-7

To a mixture of 0.20 g B-41 in 4.0 ml HCl$_{aq.}$ 0.1 N solution 0.5 ml of THF are added at room temperature. The brown suspension is stirred for 6 h at 60° C. The mixture is then evaporated to dryness and the residue was suspended in water. The brown precipitate is filtrated off and dried in the vacuum at 25° C. 0.12 g of the desired product are isolated as a brown-red powder.

$^1$H-NMR (DMSO, 360 MHz): 14.36 (s, 1H); 10.75 (s, 1H); 8.35 (s, 1H); 7.70 (s, 1H); 7.63 (d, 1H); 7.37 (d, 1H); 4.15 (t, 2H); 2.21 (s, 3H); 1.67-1.61 (m, 2H); 0.87 (t, 3H).

SYNTHESIS EXAMPLE (12)

Preparation of B-41

Compound B-38 (490 mg) is dissolved in 2.0 ml of pyridine at room temperature. 0.154 ml of acetic anhydride are added dropwise and the brown solution is stirred for 1 h at 25° C. Then the mixture is added to 5.0 ml of ice-water and stirred for 30 min at 15° C. The yellow precipitate is filtrated off, washed with water and dried in the vacuum at 30° C. 0.33 g of the desired product are isolated as a yellow powder.

$^1$H-NMR (DMSO, 360 MHz): 8.40 (s, 1H); 7.85 (d, 1H); 7.60 (d, 1H); 7.54 (s, 1H); 4.25 (t, 2H); 3.53-3.50 (m, 3H); 2.30 (s, 3H); 1.88 (s, 3H); 1.81-1.71 (m, 2H); 1.15 (t, 3H); 0.98 (t, 3H).

The invention claimed is:

1. A body-care formulation comprising about 5 to about 10000 ppm, based on the total formulation of a benzotropolone derivatives of formula (1) therein

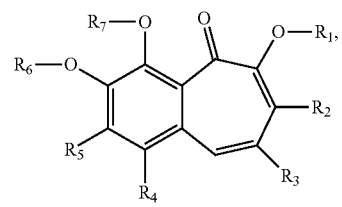

wherein
$R_1$, $R_2$ and $R_7$ independently from each other are hydrogen; $C_1$-$C_3$alkyl; or $COR_8$;
$R_3$ is hydrogen; or $COOR_9$;
$R_4$ is hydrogen; or $C_1$-$C_{30}$ alkyl;
$R_5$ is hydrogen; hydroxy; $C_1$-$C_3$-alkoxy; or —O—(CO)—$R_{10}$;
$R_6$ is hydrogen; $C_1$-$C_{30}$alkyl; or $COR_8$; or
$R_5$ and $R_6$ together may form a five or six membered ring; or
$R_6$ and $R_7$ together form a five or six membered ring; and
$R_8$, $R_9$, $R_{10}$ independently of each other are $C_1$-$C_{30}$alkyl.
2. The body-care formulation according to claim 1, wherein
$R_1$ is hydrogen; $COR_8$; or $C_1$-$C_{30}$alkyl;
$R_2$, $R_4$ and $R_5$ are hydrogen;
$R_3$ is $COOR_9$;
$R_6$ and $R_7$ independently from each other are hydrogen; $C_1$-$C_{30}$alkyl; or $COR_8$; or
$R_6$ and $R_7$ together form a five or six membered ring; and
$R_8$ is defined as in claim 1.
3. The body-care product according to claim 2, wherein
$R_1$ is hydrogen; or CO—CH$_3$;
$R_2$, $R_4$ and $R_5$ are hydrogen;
$R_3$ is COO—C$_3$H$_7$;
$R_6$ and $R_7$ independently from each other are hydrogen; or CO—CH$_3$; or
$R_6$ and $R_7$ together form a five or six membered ring.

4. The body-care formulation according to claim 1, wherein

R$_1$, R$_2$ and R$_7$ independently from each other are hydrogen; methyl; or —CO—CH$_3$;

R$_3$ is hydrogen; or —COOR$_9$;

R$_4$ is hydrogen; or C$_1$-C$_{30}$alkyl;

R$_5$ is hydrogen; methoxy; or —O—(CO)—CH$_3$;

R$_6$ is hydrogen; methyl; or —CO—CH$_3$; or

R$_5$ and R$_6$ together may form a five or six membered ring; or

R$_6$ and R$_7$ together form a five or six membered ring; and

R$_9$ is C$_1$-C$_{10}$alkyl.

5. The body-care formulation according to claim 1, wherein the benzotropolones derivatives of formula (I) are selected from the group consisting of

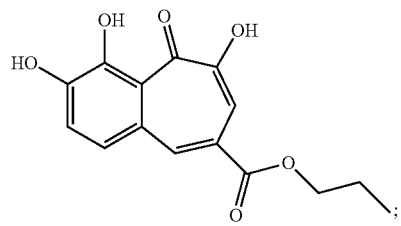
(B-1);

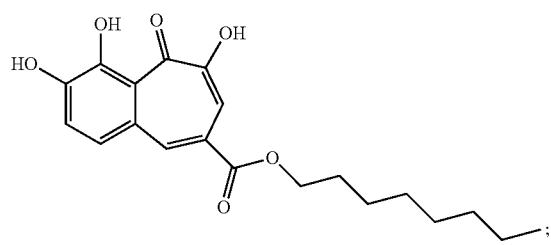
(B2);

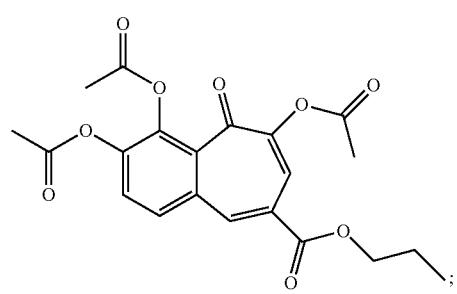
(B-5);

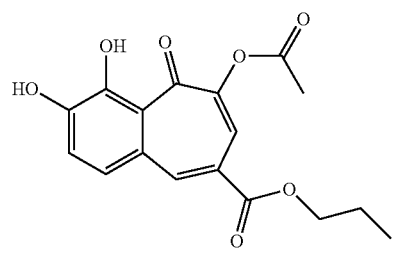
(B-7);

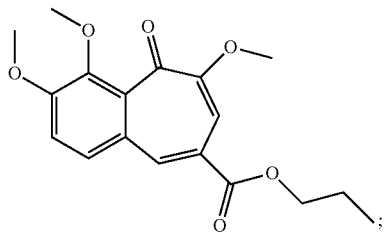
(B-14);

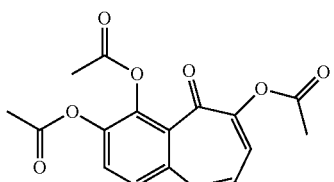
(B-18);

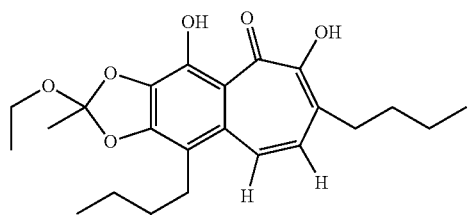
(B-20);

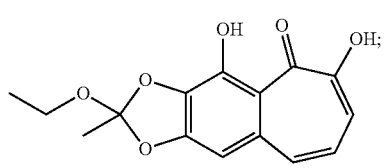
(B-23);

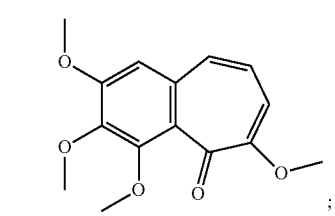
(B-29);

(B-36)

(B-41)

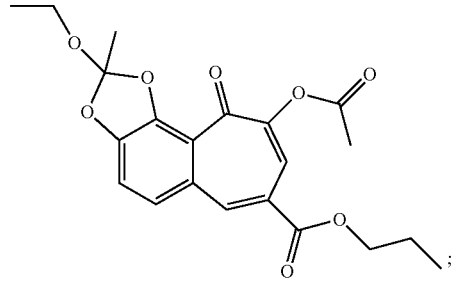

-continued (B-38)
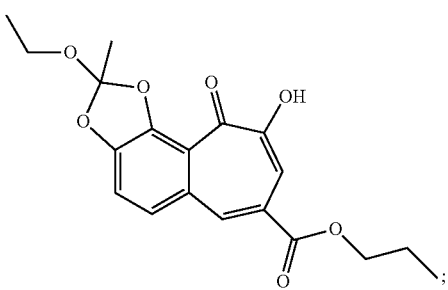

(B-39)
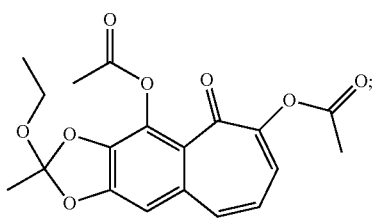

(B-44)
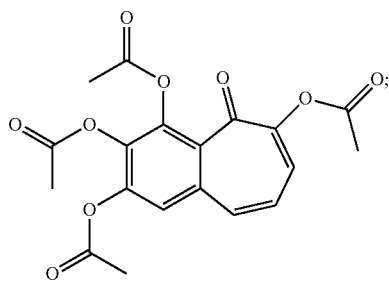

(B-45)
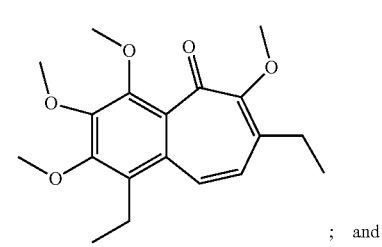
; and (B-46)
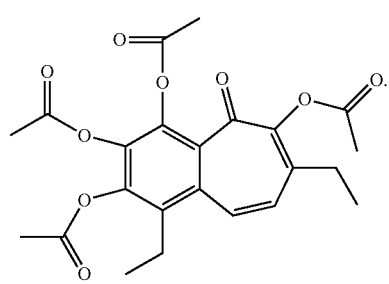

6. The body-care formulation according to claim 1, wherein the body-care product is a product for the skin and its adnexa.

7. The body-care formulation according to claim 6, wherein the body-care products are selected from skin-care products, bath and shower additives, preparations containing fragrances and odoriferous substances, hair-care products, dentifrices, deodorizing and antiperspirant preparations, decorative preparations, light protection formulations and preparations containing active ingredients.

8. The body-care formulation according to claim 6, wherein the body-care products are selected from body oils, body lotions, body gels, treatment creams, skin protection ointments, shaving preparations and skin powders.

9. The body-care formulation according to claim 6, wherein the body-care products contain fragrances and odoriferous substances which are selected from scents, perfumes, toilet waters and shaving lotions.

10. The body-care formulation according to claim 6, wherein the body-care products are hair-care products and are selected from shampoos, hair conditioners, products for styling and treating hair, perming agents, hair sprays and lacquers, hair gels, hair fixatives and hair dyeing or bleaching agents.

11. The body-care formulation according to claim 6, wherein the body-care products are decorative preparations and are selected from lipsticks, nail varnishes, eye shadows, mascaras, dry and moist make-up, rouge, powders, depilatory agents and suntan lotions.

12. The body-care formulation according to claim 6, wherein the body-care products contain active ingredients and are selected from hormone preparations, vitamin preparations, vegetable extract preparations and antibacterial preparations.

13. The body-care formulation according to claim 1, wherein the benzotropolone derivative of formula (1) is formula (4')
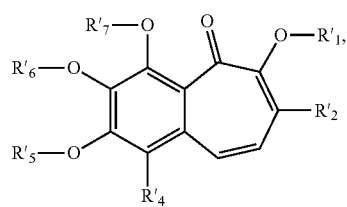

wherein
$R'_2$ and $R'_4$ independently from each other are $C_1$-$C_{30}$alkyl;
$R'_1$, $R'_5$, $R'_6$ and $R'_7$ are $C_1$-$C_{30}$alkyl; or $COR_8$.

14. The body-care formulation according to claim 1, wherein the benzotropolone of formula (1) is formula (5')
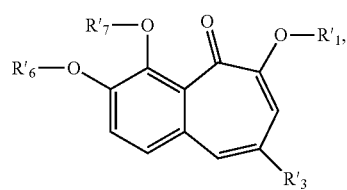

wherein
$R'_3$ is a radical of formula

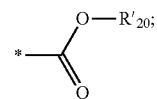

$R'_{20}$ is $C_3$-$C_{30}$alkyl;
$R'_1$, $R'_6$ and $R'_7$ are hydrogen; $COR_9$; or $C_1$-$C_{30}$alkyl; and
$R'_9$ is $C_1$-$C_{30}$alkyl.

15. The body-care formulation according to claim 1 comprising therein anyone of the compounds selected from the group consisting of formulae (1'), (2'), (3'), (4') and (5')

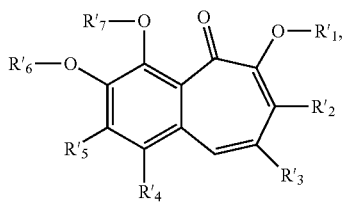

(1')

wherein
R'$_1$, R'$_2$ and R'$_7$ independently from each other are hydrogen; C$_1$-C$_{30}$alkyl; or COR$_8$;
R'$_3$ is hydrogen; or COOR$_9$;
R'$_4$ is hydrogen; or C$_1$-C$_{30}$alkyl;
R'$_5$ is hydrogen; hydroxy; C$_1$-C$_{30}$-alkoxy; or —O—(CO)—R$_{10}$;
R'$_6$ is hydrogen; C$_1$-C$_{30}$alkyl; or COR$_8$; or
R'$_5$ and R'$_6$ together may form a five or six membered ring; or
R'$_6$ and R'$_7$ together form a five or six membered ring; and
R'$_8$, R'$_9$, R'$_{10}$ independently of each other are C$_1$-C$_{30}$alkyl;
with the proviso that in the compounds of formula (1') either R$_7$ and R$_8$ together form a five or six membered ring; or R$_6$ and R$_7$ together form a five or six membered ring;

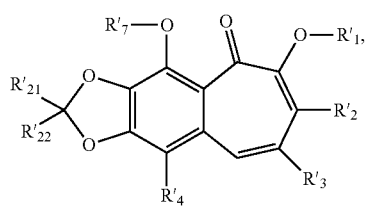

(2')

wherein
R'$_{21}$ and R'$_{22}$ independently of one another are hydrogen; OH; C$_1$-C$_{30}$alkyl; or C$_1$-C$_{30}$alkoxy, and
R'$_1$, R'$_2$, R'$_3$, R'$_4$, and R'$_7$ are defined as in formula (1');

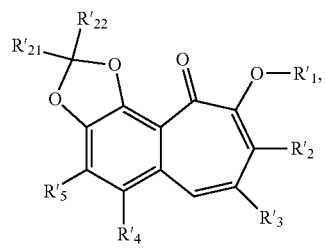

(3')

wherein
R'$_{21}$ and R'$_{22}$ independently of one another are hydrogen; OH; C$_1$-C$_{30}$alkyl; or C$_1$-C$_{30}$alkoxy; and
R'$_1$, R'$_2$, R'$_3$, R'$_4$ and R'$_5$ are defined as in formula (1');

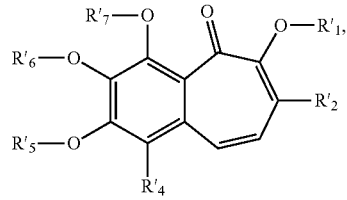

(4')

wherein
R'$_2$ and R'$_4$ independently from each other are C$_1$-C$_{30}$alkyl;
R'$_1$, R'$_5$, R'$_6$ and R'$_7$ are C$_1$-C$_{30}$alkyl; or COR$_8$; and
R'$_8$ is defined as in formula (1');

and

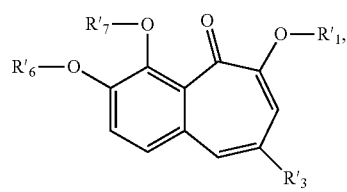

(5')

wherein
R'$_3$ is a radical of formula

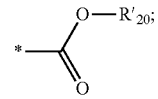

R'$_{20}$ is C$_3$-C$_{30}$alkyl;
R'$_1$, R'$_6$ and R'$_7$ are hydrogen; COR$_9$; or C$_1$-C$_{30}$alkyl; and
R'$_9$ is C$_1$-C$_{30}$alkyl.

* * * * *